(12) United States Patent
Gulevich et al.

(10) Patent No.: US 8,394,610 B2
(45) Date of Patent: Mar. 12, 2013

(54) METHOD FOR CONSTRUCTING AN OPERON CONTAINING TRANSLATIONALLY COUPLED GENES

(75) Inventors: Andrey Yurievich Gulevich, Moscow (RU); Aleksandra Yurievna Skorokhodova, Moscow (RU); Vladimir Yurievich Ermishev, Moscow (RU); Natalya Igorevna Minaeva, Moscow (RU); Danila Vadimovich Zimenkov, Moscow (RU); Aleksandr Aleksandrovich Krylov, Moscow (RU); Irina Vladimirovna Biryukova, Moscow (RU); Sergei Vladimirovich Mashko, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 656 days.

(21) Appl. No.: 12/388,568

(22) Filed: Feb. 19, 2009

(65) Prior Publication Data

US 2009/0226919 A1  Sep. 10, 2009

(30) Foreign Application Priority Data

Feb. 19, 2008 (RU) ................ 2008105793

(51) Int. Cl.
*C12N 15/64* (2006.01)
*C07H 21/04* (2006.01)

(52) U.S. Cl. ................... 435/91.4; 536/23.1

(58) Field of Classification Search ................ None
See application file for complete search history.

(56) References Cited

U.S. PATENT DOCUMENTS

| | | |
|---|---|---|
| 2005/0181488 A1 | 8/2005 | Akhverdian et al. |
| 2005/0191684 A1 | 9/2005 | Zimenkov et al. |
| 2006/0014257 A1 | 1/2006 | Katashkina et al. |
| 2006/0035348 A1 | 2/2006 | Gulevich et al. |
| 2006/0063240 A1 | 3/2006 | Katashkina et al. |
| 2008/0113416 A1 | 5/2008 | Filippov et al. |
| 2009/0087886 A1 | 4/2009 | Filippov et al. |
| 2009/0098621 A1 | 4/2009 | Rybak et al. |

OTHER PUBLICATIONS

Rex et al., J. Biol. Chemi., 269, 27, 18118-18127, 1994.*
Lindahl et al., Annual Review of Genetics, vol. 20, pp. 297-326, 1986.*
U.S. Appl. No. 11/830,969, filed Jul. 31, 2007, Gulevich et al.
U.S. Appl. No. 11/952,297, filed Dec. 7, 2007, Rybak et al.
U.S. Appl. No. 12/017,379, filed Jan. 22, 2008, Rybak et al.
U.S. Appl. No. 12/022,299, filed Jan. 30, 2008, Rybak et al.
U.S. Appl. No. 61/058,313, filed Jun. 3, 2008, Ermishev et al.
U.S. Appl. No. 12/372,060, filed Feb. 17, 2009, Gulevich et al.

* cited by examiner

*Primary Examiner* — Nancy T Vogel
(74) *Attorney, Agent, or Firm* — Shelly Guest Cermak; Cermak Nakajima LLP

(57) ABSTRACT

The present invention provides a method for constructing recombinant translationally coupled operons, a method for producing useful metabolites using the bacterium containing the coupled operons, and a method for monitoring gene expression.

11 Claims, 4 Drawing Sheets

| | | |
|---|---|---|
| C*AGGAG*ACTTTC<u>TGA</u>TG | *trpE-D* | (SEQ ID NO: 40) |
| C*GAGG*GGAAATC<u>TGA</u>TG | *trpB-A* | (SEQ ID NO: 41) |
| GC*ACGAG*GG<u>TAA</u>ATG | *trpD-C* | (SEQ ID NO: 42) |
| <u>*TAAGGA*</u>AAGGACAATG | *trpC-B* | (SEQ ID NO: 43) |
| TT*AGGAG*TC<u>TGA</u>CATG | *thrA-B* | (SEQ ID NO: 44) |
| CT*GGA*AAAC<u>TAA</u>ATG | *thrB-C* | (SEQ ID NO: 45) |
| *GGAG*TG<u>TAA</u>GAAATG | *galT-K* | (SEQ ID NO: 46) |
| AT*GGAG*<u>TGA</u>TCGCCATG | *hisG-D* | (SEQ ID NO: 47) |
| CT<u>*TAAGGAG*</u>CAAGC<u>ATGA</u> | *hisD-C* | (SEQ ID NO: 48) |
| GC*GGAG*CAAGT<u>TTGA</u> | *hisC-B* | (SEQ ID NO: 49) |
| A*AAGGAG*TGCTG<u>TAA</u>TG | *hisB-H* | (SEQ ID NO: 50) |
| CT*GGAG*ATG<u>TGA</u>TG | *hisH-A* | (SEQ ID NO: 51) |
| <u>TGA</u>*GG*AACCATG | *lgt-thyA* | (SEQ ID NO: 52) |
| <u>*TAAGGAG*</u>ATAGCAATG | *rplC-D* | (SEQ ID NO: 53) |
| *GAGGAG*ATGCTGG<u>ATGA</u> | *rplD-W* | (SEQ ID NO: 54) |
| <u>TAA</u>GTC*GGAGG*AGTAATACAATG | *rplW-B* | (SEQ ID NO: 55) |
| <u>TAA</u>TTTT*AGAGG*ATAAGCCATG | *rplB-rpsS* | (SEQ ID NO: 56) |
| <u>TAA</u>GGT*AGGAGG*AAGAGATG | *rpsS-rplV* | (SEQ ID NO: 57) |

FIG. 1

METHOD FOR CONSTRUCTING AN OPERON CONTAINING TRANSLATIONALLY COUPLED GENES

This application claims priority under 35 U.S.C. §119 to Russian Patent Application No. 2008105793, filed on Feb. 19, 2008, which is incorporated in its entirety by reference. The Sequence Listing filed herewith in electronic format is also hereby incorporated by reference in its entirety (File Name: US-350_Seq_List; File Size: 44 KB; Date Created: Feb. 19, 2009).

The instant application contains a Sequence Listing which has been submitted in ASCII format via EFS-Web and is hereby incorporated by reference in its entirety. Said ASCII copy, created on Jul. 7, 2011, is named US-350.txt and is 50,901 bytes in size.

BACKGROUND OF THE INVENTION

1. Field of Invention

The present invention relates to biotechnology and the microbiological industry, and specifically to a method for constructing an operon containing translationally coupled genes, a method for producing useful metabolites using bacteria containing the coupled genes, and a method for monitoring gene expression.

2. Description of the Related Art

Translation of genes in bacteria can be optimized using translational coupling, which is known to occur in prokaryotic cells.

It was found that *E. coli* trpE polar mutations were 10 times more polar for trpD gene expression than for downstream (trpC, B, or A) gene expression. This effect was shown to be the result of "translational coupling," in which efficient translation of the trpE-trpD intercistronic region utilizes overlapping stop and start codons. Therefore, the trpE and trpD gene products form a functional complex in the cell (Oppenheim D. S, and Yanofsky C., Genetics 95(4):785-95 (1980)).

Precise frameshift and nonsense mutations were introduced into the region preceding the galactokinase gene (galK) of *E. coli*. These mutations alter the upstream translation termination position relative to the galK translation initiation signal. Constructions were characterized that allow ribosomes to stop selectablely before, within, or downstream from the galK initiation signal. The effects of these mutations on galK expression were monitored. Galactokinase levels are highest when upstream translation terminates within the galK initiation region. In contrast, when translation stops either upstream or downstream from the galK start site, galK expression is drastically reduced. These results demonstrate that the galK gene is translationally coupled to the gene immediately preceding galK in the gal operon, that is, galT, and that the coupling effect depends primarily on the position at which upstream translation terminates relative to the galK start site (Schumperli D. et al, Cell, 30(3):865-71 (1982)).

The conditions necessary for high-level expression of methionyl bovine growth hormone (Met-bGH) in *E. coli* were investigated. Plasmids were constructed that contain a thermoinducible runaway replicon, ribosome binding sites which served as transcriptional and translational initiation sites for the expression of the bGH gene, and either the *E. coli* tryptophan or lipoprotein promoter. The expression of Met-bGH was low with either promoter. However, expression levels of up to 30% of total cell protein were obtained after the introduction of additional codons positioned 3' to the initiating AUG codon, thus altering the $NH_2$-terminal amino acid sequence of bGH. To obtain high-level expression of Met-bGH, a two-cistron system was constructed in which the codons that enhanced the expression of bGH were incorporated into the first cistron, and the coding region for Met-bGH was incorporated into the second cistron. This approach may be generally applicable to achieving high-level expression of a gene that contains $NH_2$-terminal sequences that inhibit efficient expression. Analyses of the stabilities of the bGH derivatives and their transcripts in vivo suggested that the variations in the level of expression were due to variations in the efficiency of mRNA translation (Schoner B. E. et. al., Proc. Natl. Acad. Sci. USA, 81(17): 5403-7 (1984)).

Expression of trpB and trpA on the *E. coli* tryptophan operon is shown to be "translationally coupled", i.e., efficient translation of the trpA coding region is dependent on the prior translation of the trpB coding region, and termination of translation at the trpB stop codon. To examine the dependence of trpA expression on the ribosome binding site sequence in the distal segment of trpB, deletion mutants of the trpB sequence were produced. Analysis of trpA expression in these deletion mutants established that the ribosome binding site sequence is required for efficient translation of the trpA segment of the trp mRNA. The translational effect on independent initiation at the trpA ribosome binding site was modest (Das A. and Yanofsky C., Nucleic Acids Res., 12 (11):4757-68 (1984)).

A trp-lac fusion system in which part of the trpA gene is fused to the lacZ gene was used to investigate whether translational coupling occurs between the tryptophan operon trpB and trpA genes in *E. coli*. This fusion protein has the translation initiation site of trpA but retains beta-galactosidase activity. A frameshift mutation was introduced early in trpB and its effect on transcription and translation of the trp-lac fusion was measured. The mutation resulted in a 10-fold drop in beta-galactosidase activity, but only a 2-fold drop in lacZ mRNA or galactoside transacetylase levels. An rho mutation restored the lacZ mRNA and transacetylase levels to those of the control but only increased the beta-galactosidase level to 20% of the control. These results demonstrate that if the trpB gene is not translated, efficient translation of the trpA'-lac'Z mRNA does not occur, and thus, that these genes are translationally coupled (Aksoy S. et al, J. Bacteriol., 157(2):363-7 (1984)).

The trpB and trpA coding regions of the polycistronic trp mRNA of *E. coli* are separated by overlapping translational stop and start codons. Efficient translation of the trpA coding region is subject to translational coupling, i.e., maximum trpA expression is dependent on prior translation of the trpB coding region. Previous studies have demonstrated that the trpA Shine-Dalgarno sequence (within trpB) and/or the location of the trpB stop codon influenced trpA expression. To specifically examine the effect of the location of the stop codon, plasmids were constructed in which different nucleotide sequences preceding the trpA start codon were retained, and only the reading frame was changed. When trpB translation proceeded in the wild-type reading frame and terminated at the normal trpB stop codon, trpA polypeptide levels increased as compared to the levels observed when translation stopped before or after the natural trpB stop codon. The proximity of the trpB stop codon to the trpA start codon therefore markedly influences trpA expression (Das A. and Yanofsky C., Nucleic Acids Res., 17(22):9333-40 (1989)).

A TGATG vector system was developed that allows for the construction of hybrid operons with partially overlapping genes, and which utilize translational coupling to optimize expression of the cloned cistrons in *E. coli*. In this vector system (plasmid pPR-TGATG-1), the coding region of a foreign gene is attached to the ATG codon on the vector to form a hybrid operon which is transcribed from the phage lambda PR promoter. The cloned gene is the distal cistron of this hybrid operon ('overlappon'). The efficiently translated cro'-cat'-'trpE hybrid cistron is proximal to the promoter. The coding region of this artificial fused cistron (the length of the corresponding open reading frame is about 120 amino acids (aa)), and includes the following: the N-terminal portions of phage lambda Cro protein (20 aa), the CAT protein of *E. coli* (72 aa), and 3' C-terminal codons of the *E. coli* trpE gene product. At the 3'-end of the cro'-cat'-'trpE fused cistron there is a region for efficient translation reinitiation: a Shine-Dalgarno sequence of the *E. coli* trpD gene and the overlapping stop and start codons (TGATG). In this sequence, the last G is the first nucleotide of the unique SacI-recognition site (GAGCT decreases C), and so integration of the structural part of the foreign gene into the vector plasmid may be performed using blunt-end DNA linking after the treatment of pPR-TGATG-1 with SacI and *E. coli* DNA polymerase I or its Klenow fragment (Mashko et. al., Gene, 88(1):121-6 (1990)).

But currently, there have been no reports of using a bacterium having an operon containing translationally coupled genes for the purpose of producing useful metabolites. A bacterium having translationally coupled genes can be also used to monitor the expression of the genes.

SUMMARY OF THE INVENTION

Objects of the present invention include altering the expression amounts of synthesized proteins.

The above objects were achieved by finding that constructing operons containing translationally coupled genes in a bacterium can lead to alteration of the expression amounts of the proteins encoded by the genes.

The present invention provides a bacterium having translationally coupled genes which results in altered production levels of the proteins expressed by those genes.

It is an aspect of the present invention to provide a method for constructing an operon comprising translationally coupled genes, comprising:

constructing a DNA fragment comprising an excisable gene coding for a selectable marker flanked by intercistronic regions of prokaryotic translationally coupled genes, where the first intercistronic region is located upstream of the selectable marker gene, and said region comprises the termination codon of the proximal gene on the operon, and a SD-sequence, and an initiation codon of an ORF which is formed after excising the gene coding for selectable marker, wherein the SD-sequence is located before the initiation codon and the termination codon is located before or partially overlapping with the SD-sequence;

and the second intercistronic region is located downstream of the selectable marker gene, and this region comprises a termination codon of an ORF which is formed after excising the gene coding for selectable marker, a SD-sequence for the distal gene on the operon, and initiation codon for the distal gene on the operon, wherein the SD-sequence is located before the initiation codon and the termination codon is located before or partially overlapping with the initiation codon;

integrating said DNA fragment between adjacent genes using homologous recombination; and excising the gene coding for the selectable marker by a site-specific recombination system, and as a result of said excising, an ORF coding for a peptide results between the adjacent genes.

It is a further aspect of the present invention to provide the method as described above, wherein said first intercistronic region is the intercistronic region between the genes selected from the group consisting of rplC and rplD, trpC and trpB, rplW and rplB, rplB and rpsS, rpsS and rplV, and lgt and thyA; and said second intercistronic region is the intercistronic region between the genes selected from the group consisting of trpE and trpD, trpB and trpA, trpD and trpC, trpC and trpB, thrA and thrB, thrB and thrC, galT and galK, hisG and hisD, hisB and hisH, hisH and hisA, lgt and thyA, rplC and rplD, rplW and rplB, rplB and rpsS, rpsS and rplV, hisD and hisC, hisC and hisB, and rplD and rplW, and wherein the second intercistronic region is the intercistronic region between the hisD and hisC genes, hisC and hisB genes, or rplD and rplW genes when the first nucleotide of the second codon of the distal gene is adenosine.

It is a further aspect of the present invention to provide the method as described above, wherein said first intercistronic region is the intercistronic region between the rplC and rplD genes, and said second intercistronic region is the intercistronic region between the trpE and trpD genes.

It is a further aspect of the present invention to provide the method as described above, wherein said homologous recombination in said integrating step comprises the Red-driven integration system.

It is a further aspect of the present invention to provide the method as described above, wherein said site-specific recombination system in said excising step comprises the int-xis system.

It is a further aspect of the present invention to provide the method as described above, wherein said operon is present on a plasmid or in the bacterial chromosome.

It is a further aspect of the present invention to provide the method as described above, wherein said operon is bicistronic.

It is a further aspect of the present invention to provide the method as described above, wherein said operon comprises the aroG4 and serA5 genes.

It is a further aspect of the present invention to provide the method as described above, wherein said operon is tricistronic.

It is a further aspect of the present invention to provide the method as described above, wherein said operon comprises the aroD, aroE, and aroC genes.

It is a further aspect of the present invention to provide the method as described above, wherein said operon additionally comprises an effective ribosome binding site upstream of the proximal gene.

It is a further aspect of the present invention to provide a bacterium having an operon comprising translationally coupled genes constructed by the method as described above which is present in the bacterial chromosome or on a plasmid.

It is a further aspect of the present invention to provide the bacterium as described above, wherein said bacterium belongs to the family Enterobacteriaceae.

It is a further aspect of the present invention to provide the bacterium as described above, wherein said bacterium belongs to the genus *Escherichia*.

It is a further aspect of the present invention to provide the bacterium as described above, wherein said bacterium belongs to the genus *Pantoea*.

It is a further aspect of the present invention to provide a bacterium having an operon comprising translationally coupled genes constructed by the method as described above.

It is a further aspect of the present invention to provide the bacterium as described above, wherein said bacterium has the ability to produce a useful metabolite.

It is a further aspect of the present invention to provide the bacterium as described above, wherein said useful metabolite is selected from the group consisting of native proteins, heterologous proteins, enzymes, L-amino acids, nucleosides, nucleotides, and vitamins.

It is a further aspect of the present invention to provide a method for producing a useful metabolite comprising:
cultivating the bacterium according to any of the above in a medium; and
collecting said useful metabolite from the culture medium.

It is a further aspect of the present invention to provide the method as described above, wherein said useful metabolite is selected from the group consisting of native proteins, heterologous proteins, enzymes, L-amino acids, nucleosides, nucleotides, and vitamins.

It is a further aspect of the present invention to provide a method for monitoring the expression of a gene comprising:
constructing an expression system having said gene translationally coupled with a marker gene by the method according to the above;
expressing said translationally coupled genes; and
measuring the activity of the protein coded by said marker gene.

The present invention is described in detail below.

BRIEF DESCRIPTION OF THE DRAWINGS

FIG. 1 shows sequences and organization of intercistronic regions of known translationally coupled genes. Initiation codons are depicted in bold; SD-sequences are depicted in bold italic, termination codons are depicted in underlined bold.

DETAILED DESCRIPTION OF THE PREFERRED EMBODIMENTS

Figure 2:
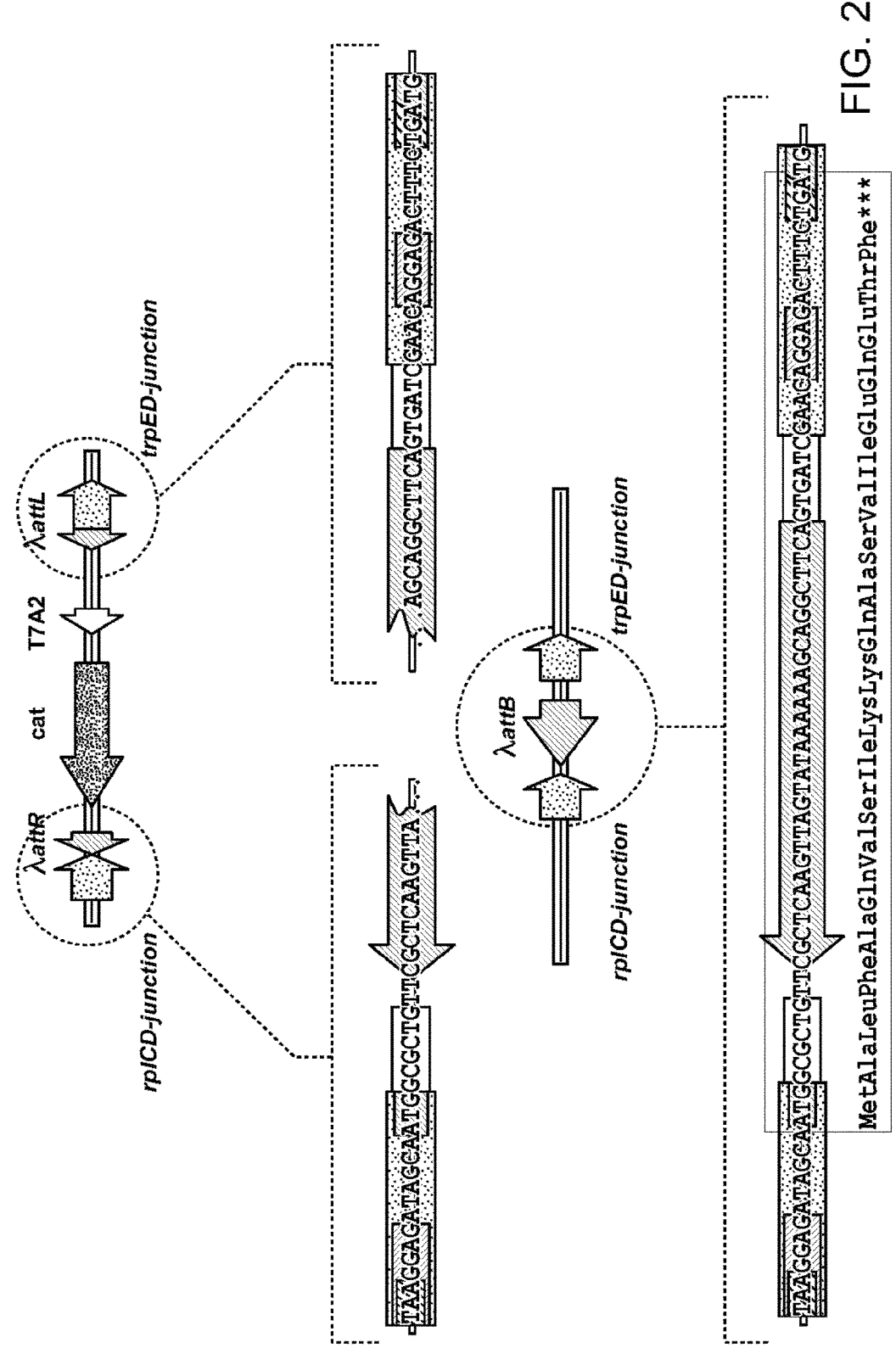
FIG. 2 shows organization of the DNA fragment before excision of the gene coding for the selectable marker (1) (SEQ ID NO: 73 and 74), and the DNA construct which remains after excision of the gene (2) (SEQ ID NO: 75 and 76).

1. Method for Constructing an Artificial Operon with Translationally Coupled Genes The method of the present invention is a method for constructing an artificial operon containing translationally coupled genes.

The phrase "translational coupling" means that efficient translation of the distal gene (downstream) in the operon is dependent on the prior translation of the proximal gene (upstream) in the operon. More specifically, the distal cistron is inaccessible to the free initiating ribosome subunits, and only ribosome subunits which terminate at the proximal cistron can effect initiation. Under ideal conditions, transcription and translation of the operon having the translationally coupled genes leads to accumulation of equimolar amounts of the proteins encoded by the genes.

The operon is an artificial operon in which the genes present on the operon are translationally coupled. The operon may contain two or more genes. It could be a completely artificial operon with the gene(s) originally located in the different places on the chromosome, geterological genes, or a combination thereof. It could also be an operon constructed from the native operon in which the genes of the operon were not translationally coupled. It could also be an operon constructed from two adjacent genes originally located on the chromosome, and does not make up any operon. When the operon is used in a bacterium to produce a useful metabolite, it is suitable to construct the operon containing genes coding for the enzymes involved in the biosynthesis of the useful metabolite. When the operon is used for quantitative analysis of gene expression, a marker gene should be translationally coupled to the gene being studied.

To translationally couple the genes on the operon, a specific DNA fragment containing a selectable marker gene is constructed as described below, and then this fragment is integrated between the genes to be translationally coupled, and the selectable marker gene is excised from the construct. Due to the specific organization of the DNA fragment, excision of the selectable marker gene leads to formation of an ORF coding for a short nonsense peptide. After excision of the selectable marker gene, the ORF in the construct coding for the short peptide is translationally coupled to both the proximal (first) gene and the distal (second) gene on the operon. As a result, the proximal and distal genes on the operon become translationally coupled.

The DNA fragment contains an excisable gene coding for a selectable marker flanked by intercistronic regions of the prokaryotic translationally coupled genes, where:
the first intercistronic region is located upstream of the selectable marker gene, and said region contains the termination codon of the proximal gene on the operon, and a SD-sequence and an initiation codon of an ORF which is formed after excising the gene coding for the selectable marker, wherein the SD-sequence is located before the initiation codon and the termination codon is located before or partially overlapping with the SD-sequence,
the second intercistronic region is located downstream of the selectable marker gene, and this region contains a termination codon of an ORF which is formed after excising the gene coding for selectable marker, a SD-sequence for the distal gene on the operon, and initiation codon for the distal gene on the operon, wherein the SD-sequence is located before the initiation codon and the termination codon is located before or partially overlapping with the initiation codon.

The phrase "gene coding for a selectable marker" means any gene which can be used for selection of the DNA fragment. It can be a gene which confers resistance to an antibiotic, such as chloramphenicol, kanamycin, ampicillin, tetracycline etc. The gene coding for the selectable marker is flanked on either side by two sites which allow for a site-specific integration/excision system. Examples of such systems include phage systems, such as the Int/Xis system of phage lambda (Datsenko, K. A. and Wanner, B. L., Proc. Natl. Acad. Sci. USA, 97, 12, p. 6640-6645 (2000)), the cre/loxP system of phage P1 (Buchholz, F. et al, Nucleic Acids Res., 24, 21, p. 4256-4262 (1996)), the Flp/FRT system of S. cerevisae (Huang, L. C. et al, J. Bacteriol., 179, 19, p. 6076-6083 (1997)), and the like.

The phrase "intercistronic regions of prokaryotic translationally coupled genes" means the intercistronic regions between genes in prokaryotes, such as phages and bacteria, in which translational coupling of neighboring, or adjacent genes, occurs. Generally, an intercistronic region is the distance between the termination codon of one gene and the initiation codon of the next gene. Specifically, examples of intercistronic regions of the present invention include the intercistronic region between the trpE-trpD genes, trpB-trpA genes, trpD-trpC genes, trpC-trpB genes, thrA-thrB genes, thrB-thrC genes, galT-galK genes, hisG-hisD genes, hisB-hisH genes, hisH-hisA genes, lgt-thyA genes, rplC-rplD genes, rplW-rplB genes, rplB-rpsS genes, and rpsS-rplV genes. Specifically, when the first nucleotide of the second codon of the distal gene is adenosine, the intercistronic regions between the hisD-hisC genes, hisC-hisB genes, and rplD-rplW genes can also be used. Sequences and organization of the above intercistronic regions are shown in FIG. 1 and in the Sequence listing (SEQ ID NOs: 40-57).

The method is universal, in that the method can be used to translationally couple any genes regardless of the nucleotide sequences at their 5'-end or 3'-end. This is because the DNA fragment is integrated exactly between the two genes to be translationally coupled without changing the coding regions of the genes. Such universality was achieved by constructing the first intercistronic region of the DNA fragment in such a way that it contains the termination codon of the proximal gene on the operon, a SD-sequence and the initiation codon, with the termination codon located before or partially overlapping with the initiation codon. Intercistronic regions between the rplC-rplD genes, trpC-trpB genes, rplW-rplB genes, rplB-rpsS genes, rpsS-rplV and lgt-thyA genes genes satisfy the above requirement and can be used for constructing the first intercistronic region of the DNA fragment. As the second intercistronic region of the DNA fragment, any of the intercistronic regions listed in the previous paragraph can be used.

The term "SD-sequence" means a Shine-Dalgarno sequence. A Shine-Dalgarno sequence is the signal sequence for the initiation of protein biosynthesis (translation) in bacterial mRNA. It is located 5' of the first coding AUG-codon, and consists primarily, but not exclusively, of purines. Examples of SD-sequences are indicated in FIG. 1 by bold italic characters.

Integration of the DNA fragment between two adjacent genes can occur by the homologous recombination system. Systems for homologous recombination include the Red-mediated system of phage lambda (Datsenko, K. A. and Wanner, B. L., Proc. Natl. Acad. Sci. USA, 97, 12, p 6640-6645 (2000)), recBC/sbcB system (Winans, S. C. et al, J. Bacteriol., 161, 3, p. 1219-1221 (1985)), and the like.

An example of the organization of the DNA fragment is shown in FIG. 2, wherein this fragment contains two intercistronic regions, rplC-rplD and trpE-trpD, before excision of the gene coding for the selectable marker (1), and the DNA construct which remains after excision of the gene (2). An example of the nucleotide sequence of the DNA fragment which remains after excision of the gene coding for the selection marker is shown in the Sequence Listing (SEQ ID NOs: 58). An example of the amino acid sequence of the short peptide formed after excision of selection marker gene is shown in the Sequence Listing (SEQ ID NOs: 59).

The method can be used for the translational coupling of genes both on a plasmid and in the chromosome of a bacterium.

Translational coupling of more than two genes of the artificial operon can be provided by repeating the above procedure several times. To avoid integration of the DNA fragment into the location created during the previous procedure of translational coupling, it is necessary to vary several nucleotides in the first and second intercistronic regions of the DNA fragment. The preferable position for the variation of the nucleotides (preferably six nucleotides) is the position after the initiation codon in the first intercistronic region and the position before the SD-sequence in the second intercistronic region of the DNA fragment. An example of these regions is depicted in FIG. 2 in the white boxes.

The particular example shown herein is the construction of an operon with two translationally coupled genes, aroG4 and serA5. The aroG4 gene (Kikuchi Y. et. al., Appl. And Env. Microb., 761-2 (1997)) is a mutant allele of aroG, which encodes 3-deoxy-D-arabinoheptulosonate-7-phosphate synthetase which is not subject to feedback inhibition by phenylalanine. A mutant aroG gene (aroG4) in which the L-proline at position 150 is replaced by L-leucine is preferred. The nucleotide sequence of the wild-type aroG gene and the amino acid sequence of the protein encoded by the aroG gene are shown in SEQ ID NO: 36 and SEQ ID NO: 37, respectively.

The gene serA5 (U.S. Pat. No. 6,180,373) is a mutant allele of serA, which encodes phosphoglycerate dehydrogenase which is not subject to feedback inhibition by serine. The Tyr at position 410 of the mutant serA gene (serA5) is deleted. The nucleotide sequence of the wild-type serA gene and the amino acid sequence of phosphoglycerate dehydrogenase encoded by the serA gene are shown in SEQ ID NO: 38 and SEQ ID NO: 39, respectively.

Figure 3:
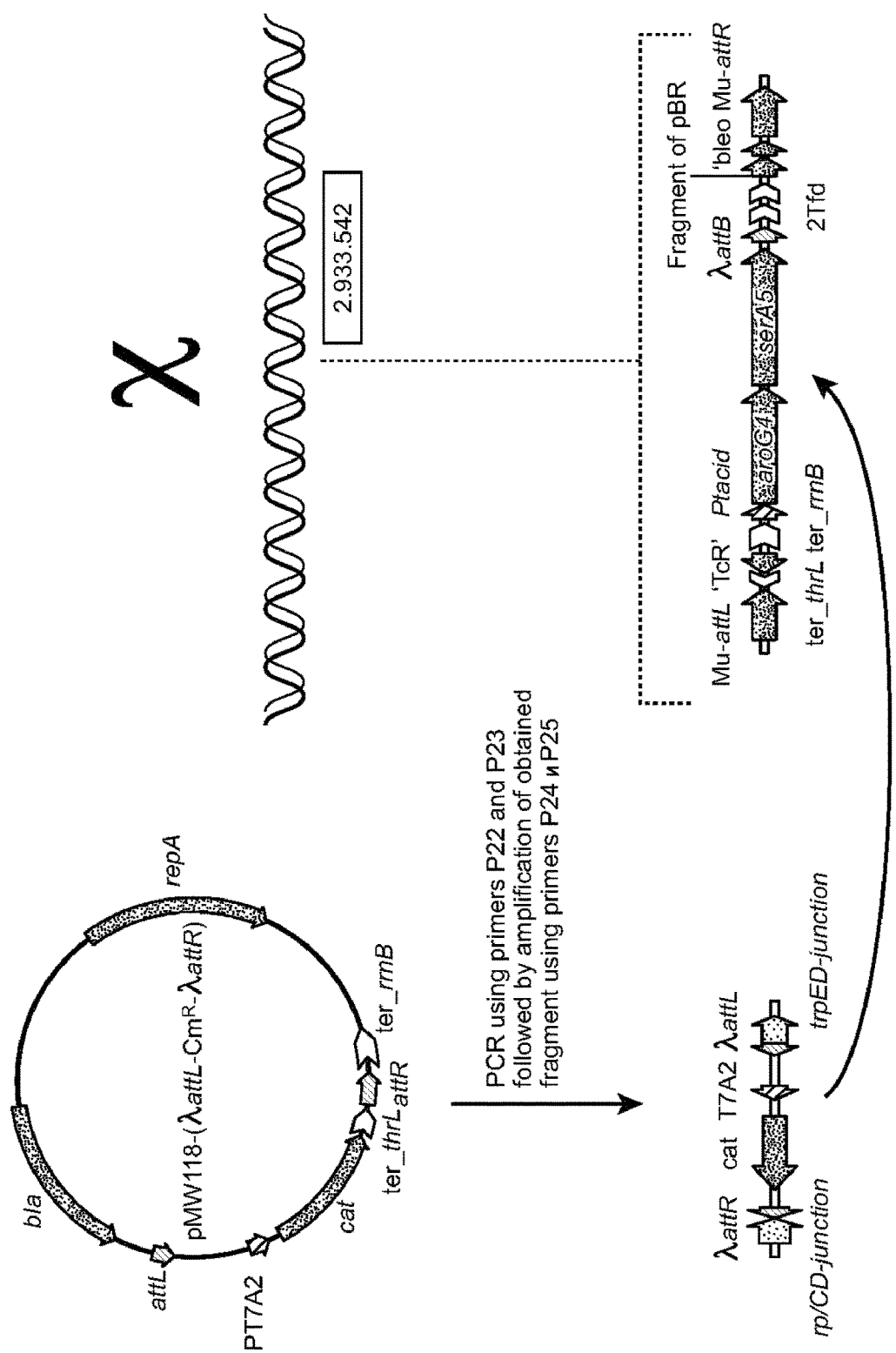
FIG. 3 shows the construction for translational coupling of the aroG4 and serA5 genes.
Figure 3:
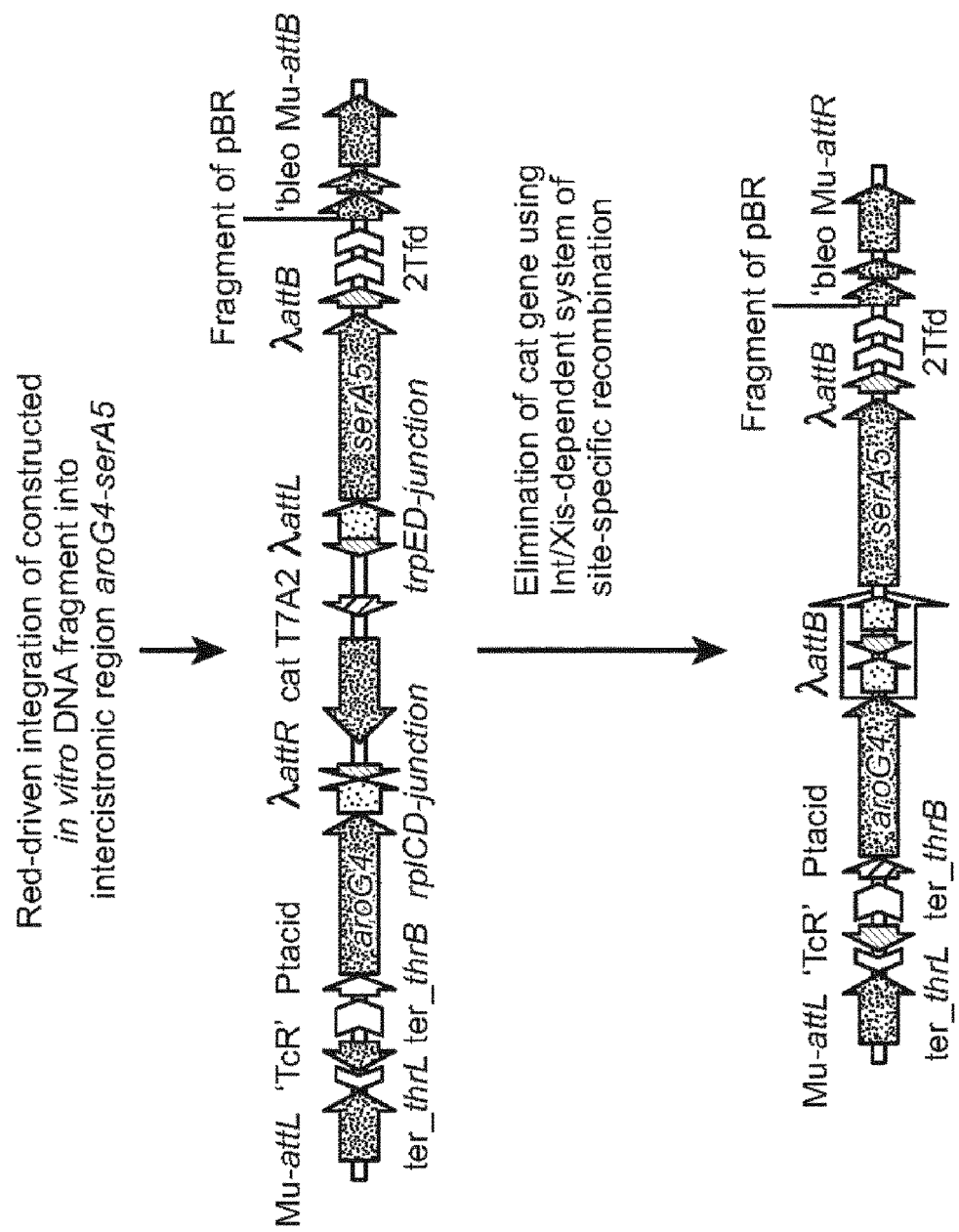

The scheme for translational coupling of aroG4 and serA5 genes is depicted in FIG. 3 and described in detail in the Examples. Translational coupling of another pair of genes, the zwf and edd genes, is also described in detail in the Examples.

Methods for preparation of plasmid DNA, digestion and ligation of DNA, transformation, selection of an oligonucleotide as a primer, and the like may be ordinary methods well-known to one skilled in the art. These methods are described, for instance, in Sambrook, J., Fritsch, E. F., and Maniatis, T., "Molecular Cloning: A Laboratory Manual, Second Edition", Cold Spring Harbor Laboratory Press (1989).

2. Bacterium of the Present Invention

The bacterium may be of the Enterobacteriaceae family, wherein the bacterium has been modified to have translationally coupled target genes on an operon.

The term "useful metabolite" includes native or recombinant proteins, enzymes, L-amino acids, nucleosides, nucleotides, and vitamins. L-amino acids include L-alanine, L-arginine, L-asparagine, L-aspartic acid, L-cysteine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine and L-valine, and preferably include aromatic L-amino acids, such as L-tryptophan, L-phenylalanine, and L-tyrosine. Nucleosides include purines and pyrimidines, such as adenosine, cytosine, inosine, guanosine, thymidine, uracil and xanthosine. Nucleotides include phosphorylated nucleosides, preferably 5'-phosphorylated nucleosides, such as 2'-deoxyadenosine-5'-monophosphate (dAMP), 2'-deoxycytidine-5'-monophosphate (dCMP), 2'-deoxyguanosine 5'-monophosphate (dGMP), thymidine-5'-monophosphate (dTMP), adenosine-5'-monophosphate (AMP), cytidine-5'-monophosphate (CMP), guanosine 5'-monophosphate (GMP), inosine 5'-monophosphate (IMP), uridine-5'-phosphate (UMP), and xanthosine-5'-monophosphate (XMP).

The term "L-amino acid-producing bacterium" means a bacterium which is able to produce and cause accumulation of an L-amino acid in a culture medium in an amount larger than a wild-type or parental strain of *E. coli*, such as *E. coli* K-12, and preferably means that the microorganism is able to cause accumulation in a medium of an amount not less than 0.5 g/L, more preferably not less than 1.0 g/L, of the target L-amino acid. The term "L-amino acid" includes L-threonine, L-lysine, L-glutamic acid, L-tryptophan, and L-histidine.

The term "nucleoside producing ability" means the ability to produce and accumulate a nucleoside in a medium. The term "having nucleoside producing ability" means that the microorganism belonging to the genus *Escherichia* is able to produce and cause accumulation of a nucleoside in a medium in amount larger than a wild-type strain of *E. coli*, such as *E. coli* W3110 and MG 1655 strains.

The Enterobacteriaceae family includes bacteria belonging to the genera *Escherichia*, *Enterobacter*, *Erwinia*, *Klebsiella*, *Pantoea*, *Photorhabdus*, *Providencia*, *Salmonella*, *Serratia*, *Shigella*, *Morganella*, *Yersinia*, etc. Specifically, those classified into the *Enterobacteriaceae* according to the taxonomy used by the NCBI (National Center for Biotechnology Information) database (http://www.ncbi.nlm.nih.gov/htbinpost/Taxonomy/wgetorg?mode=Tree&id=1236&lvl=3&keep=1&srchmode=1&unlock) can be used. A bacterium belonging to the genus *Escherichia* or *Pantoea* is preferred.

The phrase "a bacterium belonging to the genus *Escherichia*" means that the bacterium is classified into the genus *Escherichia* according to the classification known to a person skilled in the art of microbiology. Examples of a bacterium belonging to the genus *Escherichia* include, but are not limited to, *Escherichia coli* (*E. coli*).

The bacterium belonging to the genus *Escherichia* is not particularly limited, however for example, bacteria described by Neidhardt, F. C. et al. (*Escherichia coli* and *Salmonella typhimurium*, American Society for Microbiology, Washington D.C., 1208, Table 1) are encompassed.

The phrase "a bacterium belonging to the genus *Pantoea*" means that the bacterium is classified as the genus *Pantoea* according to the classification known to a person skilled in the art of microbiology. Some species of *Enterobacter agglomerans* have been recently re-classified into *Pantoea agglomerans*, *Pantoea ananatis*, *Pantoea stewartii* or the like, based on the nucleotide sequence analysis of 16S rRNA, etc. (Int. J. Syst. Bacteriol., 43, 162-173 (1993)).

L-Amino Acid-Producing Bacteria

As a bacterium which is modified to have translationally coupled genes on an operon essential for the L-amino acid production, bacteria which are able to produce either an aromatic or a non-aromatic L-amino acids may be used.

The bacterium can be obtained by construction of translationally coupled genes on an operon, and the genes are essential for the L-amino acid production in a bacterium which inherently has the ability to produce L-amino acids. Alternatively, the bacterium can be obtained by imparting the ability to produce L-amino acids to a bacterium already having translationally coupled genes on an operon, and the genes are essential for the L-amino acid production.

L-Threonine-Producing Bacteria

Examples of parent strains which can be used to derive L-threonine-producing bacteria include, but are not limited to, strains belonging to the genus *Escherichia*, such as *E. coli* TDH-6/pVIC40 (VKPM B-3996) (U.S. Pat. No. 5,175,107, U.S. Pat. No. 5,705,371), *E. coli* 472T23/pYN7 (ATCC 98081) (U.S. Pat. No. 5,631,157), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner et al., Genetika (in Russian), 14, 947-956 (1978)), *E. coli* VL643 and VL2055 (EP 1149911 A), and the like.

The strain TDH-6 is deficient in the thrC gene and tdh gene, as well as being sucrose-assimilative, and the ilvA gene has a leaky mutation. This strain also has a mutation in the rhtA gene, which imparts resistance to high concentrations of threonine or homoserine. The strain B-3996 contains the plasmid pVIC40 which was obtained by inserting a thrA*BC operon which includes a mutant thrA gene into a RSF1010-derived vector. This mutant thrA gene encodes aspartokinase homoserine dehydrogenase I which is substantially desensitized to feedback inhibition by threonine. The strain B-3996 was deposited on Nov. 19, 1987 in the All-Union Scientific Center of Antibiotics (Russia, 117105 Moscow, Nagatinskaya Street 3-A) under the accession number RIA 1867. The strain was also deposited in the Russian National Collection of Industrial Microorganisms (VKPM) (Russia, 117545 Moscow, 1$^{st}$ Dorozhny proezd, 1) on Apr. 7, 1987 under the accession number B-3996.

*E. coli* VKPM B-5318 (EP 0593792B) may also be used as a parent strain to derive L-threonine-producing bacteria. The strain B-5318 is prototrophic with regard to isoleucine, and a temperature-sensitive lambda-phage C1 repressor and PR promoter replaces the regulatory region of the threonine operon in plasmid pVIC40. The strain VKPM B-5318 was deposited in the Russian National Collection of Industrial Microorganisms (VKPM) on May 3, 1990 under accession number of VKPM B-5318.

Preferably, the bacterium is additionally modified to enhance expression of one or more of the following genes:

the mutant thrA gene which codes for aspartokinase homoserine dehydrogenase I resistant to feed back inhibition by threonine;

the thrB gene which codes for homoserine kinase;

the thrC gene which codes for threonine synthase;

the rhtA gene which codes for a putative transmembrane protein;

the asd gene which codes for aspartate-α-semialdehyde dehydrogenase; and the aspC gene which codes for aspartate aminotransferase (aspartate transaminase);

The thrA gene which encodes aspartokinase homoserine dehydrogenase I of *Escherichia coli* has been elucidated (nucleotide positions 337 to 2799, GenBank accession NC_000913.2, gi: 49175990). The thrA gene is located between the thrL and thrB genes on the chromosome of *E. coli* K-12. The thrB gene which encodes homoserine kinase of *Escherichia coli* has been elucidated (nucleotide positions 2801 to 3733, GenBank accession NC_000913.2, gi: 49175990). The thrB gene is located between the thrA and thrC genes on the chromosome of *E. coli* K-12. The thrC gene which encodes threonine synthase of *Escherichia coli* has been elucidated (nucleotide positions 3734 to 5020, GenBank accession NC_000913.2, gi: 49175990). The thrC gene is located between the thrB gene and the yaaX open reading frame on the chromosome of *E. coli* K-12. All three genes function as a single threonine operon. To enhance expression of the threonine operon, the attenuator region which affects the transcription is desirably removed from the operon (WO2005/049808, WO2003/097839).

A mutant thrA gene which codes for aspartokinase homoserine dehydrogenase I resistant to feedback inhibition by threonine, as well as the thrB and thrC genes, can be obtained as one operon from the well-known plasmid pVIC40 which is present in the threonine-producing *E. coli* strain VKPM B-3996. Plasmid pVIC40 is described in detail in U.S. Pat. No. 5,705,371.

The rhtA gene exists at 18 min on the *E. coli* chromosome close to the glnHPQ operon, which encodes components of the glutamine transport system. The rhtA gene is identical to ORF1 (ybiF gene, nucleotide positions 764 to 1651, GenBank accession number AAA218541, gi: 440181) and is located between the pexB and ompX genes. The unit expressing a protein encoded by the ORF1 has been designated the rhtA gene (rht: resistance to homoserine and threonine). Also, it was revealed that the rhtA23 mutation is an A-for-G substitution at position-1 with respect to the ATG start codon (ABSTRACTS of the 17$^{th}$ International Congress of Biochemistry and Molecular Biology in conjugation with Annual Meeting of the American Society for Biochemistry and Molecular Biology, San Francisco, Calif. Aug. 24-29, 1997, abstract No. 457, EP 1013765 A).

The asd gene of *E. coli* has already been elucidated (nucleotide positions 3572511 to 3571408, GenBank accession NC_000913.1, gi: 16131307), and can be obtained by PCR (polymerase chain reaction; refer to White, T. J. et al., Trends Genet., 5, 185 (1989)) utilizing primers prepared based on the nucleotide sequence of the gene. The asd genes of other microorganisms can be obtained in a similar manner.

Also, the aspC gene of *E. coli* has already been elucidated (nucleotide positions 983742 to 984932, GenBank accession NC_000913.1, gi: 16128895), and can be obtained by PCR. The aspC genes of other microorganisms can be obtained in a similar manner.

L-Lysine-Producing Bacteria

Examples of L-lysine-producing bacteria belonging to the genus *Escherichia* include mutants having resistance to an L-lysine analogue. The L-lysine analogue inhibits growth of bacteria belonging to the genus *Escherichia*, but this inhibition is fully or partially desensitized when L-lysine is present in the medium. Examples of the L-lysine analogue include, but are not limited to, oxalysine, lysine hydroxamate, S-(2-aminoethyl)-L-cysteine (AEC), γ-methyllysine, α-chlorocaprolactam, and so forth. Mutants having resistance to these lysine analogues can be obtained by subjecting bacteria belonging to the genus *Escherichia* to a conventional artificial mutagenesis treatment. Specific examples of bacterial strains useful for producing L-lysine include *Escherichia coli* AJ11442 (FERM BP-1543, NRRL B-12185; see U.S. Pat. No. 4,346,170) and *Escherichia coli* VL611. In these microorganisms, feedback inhibition of aspartokinase by L-lysine is desensitized.

The strain WC196 may be used as an L-lysine producing bacterium of *Escherichia coli*. This bacterial strain was bred by conferring AEC resistance to the strain W3110, which was derived from *Escherichia coli* K-12. The resulting strain was designated *Escherichia coli* AJ13069 strain and was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994 and received an accession number of FERM P-14690. Then, it was converted to an international deposit under the provisions of the Budapest Treaty on Sep. 29, 1995, and received an accession number of FERM BP-5252 (U.S. Pat. No. 5,827,698).

Examples of parent strains which can be used to derive L-lysine-producing bacteria also include strains in which expression of one or more genes encoding an L-lysine biosynthetic enzyme are enhanced. Examples of such genes include, but are not limited to, genes encoding dihydrodipicolinate synthase (dapA), aspartokinase (lysC), dihydrodipicolinate reductase (dapB), diaminopimelate decarboxylase (lysA), diaminopimelate dehydrogenase (ddh) (U.S. Pat. No. 6,040,160), phosphoenolpyrvate carboxylase (ppc), aspartate semialdehyde dehydrogenease (asd), and aspartase (aspA) (EP 1253195 A). In addition, the parent strains may have an increased level of expression of the gene involved in energy efficiency (cyo) (EP 1170376 A), the gene encoding nicotinamide nucleotide transhydrogenase (pntAB) (U.S. Pat. No. 5,830,716), the ybjE gene (WO2005/073390), or combinations thereof.

Examples of parent strains which can be used to derive L-lysine-producing bacteria also include strains having decreased or eliminated activity of an enzyme that catalyzes a reaction which generates a compound other than L-lysine by branching off from the biosynthetic pathway of L-lysine. Examples of such enzymes include homoserine dehydrogenase, lysine decarboxylase (U.S. Pat. No. 5,827,698), and the malic enzyme (WO2005/010175).

L-Cysteine-Producing Bacteria

Examples of parent strains which can be used to derive L-cysteine-producing bacteria include, but are not limited to, strains belonging to the genus *Escherichia*, such as *E. coli* JM15 which is transformed with different cysE alleles coding for feedback-resistant serine acetyltransferases (U.S. Pat. No. 6,218,168, Russian patent application 2003121601); *E. coli* W3110 having over-expressed genes which encode proteins suitable for secreting substances toxic for cells (U.S. Pat. No. 5,972,663); *E. coli* strains having lowered cysteine desulfohydrase activity (JP11155571A2); *E. coli* W3110 with increased activity of a positive transcriptional regulator for the cysteine regulon encoded by the cysB gene (WO0127307A1), and the like.

L-Leucine-Producing Bacteria

Examples of parent strains which can be used to derive L-leucine-producing bacteria include, but are not limited to, strains belonging to the genus *Escherichia*, such as *E. coli* strains resistant to leucine (for example, the strain 57 (VKPM B-7386, U.S. Pat. No. 6,124,121)) or leucine analogs including β-2-thienylalanine, 3-hydroxyleucine, 4-azaleucine, 5,5,5-trifluoroleucine (JP 62-34397 B and JP 8-70879 A); *E. coli* strains obtained by the gene engineering method described in WO96/06926; *E. coli* H-9068 (JP 8-70879 A), and the like.

The bacterium may be improved by enhancing the expression of one or more genes involved in L-leucine biosynthesis. Examples include genes of the leuABCD operon, which are preferably represented by a mutant leuA gene coding for isopropylmalate synthase not subject to feedback inhibition by L-leucine (U.S. Pat. No. 6,403,342). In addition, the bacterium may be improved by enhancing the expression of one or more genes coding for proteins which excrete L-amino acid from the bacterial cell. Examples of such genes include the b2682 and b2683 genes (ygaZH genes) (EP 1239041 A2).

L-Histidine-Producing Bacteria

Examples of parent strains which can be used to derive L-histidine-producing bacteria include, but are not limited to, strains belonging to the genus *Escherichia*, such as *E. coli* strain 24 (VKPM B-5945, RU2003677); *E. coli* strain 80 (VKPM B-7270, RU2119536); *E. coli* NRRL B-12116-B12121 (U.S. Pat. No. 4,388,405); *E. coli* H-9342 (FERM BP-6675) and H-9343 (FERM BP-6676) (U.S. Pat. No. 6,344,347); *E. coli* H-9341 (FERM BP-6674) (EP1085087); *E. coli* AI80/pFM201 (U. S. Pat. No. 6,258,554) and the like.

Examples of parent strains which can be used to derive L-histidine-producing bacteria also include strains in which expression of one or more genes encoding an L-histidine biosynthetic enzyme are enhanced. Examples of such genes include genes encoding ATP phosphoribosyltransferase (hisG), phosphoribosyl AMP cyclohydrolase (hisI), phosphoribosyl-ATP pyrophosphohydrolase (hisIE), phosphoribosylformimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that the L-histidine biosynthetic enzymes encoded by hisG and hisBHAFI are inhibited by L-histidine, and therefore an L-histidine-producing ability can also be efficiently enhanced by introducing a mutation conferring resistance to the feedback inhibition into ATP phosphoribosyltransferase (Russian Patent Nos. 2003677 and 2119536).

Specific examples of strains having an L-histidine-producing ability include *E. coli* FERM-P 5038 and 5048 into which a vector carrying a DNA encoding an L-histidine-biosynthetic enzyme (JP 56-005099 A) has been introduced, *E. coli* strains in which rht has been introduced, which is a gene for an amino acid-export (EP1016710A), *E. coli* 80 strain imparted with sulfaguanidine, DL-1,2,4-triazole-3-alanine, and streptomycin-resistance (VKPM B-7270, Russian Patent No. 2119536), and so forth.

L-Glutamic Acid-Producing Bacteria

Examples of parent strains which can be used to derive L-glutamic acid-producing bacteria include, but are not limited to, strains belonging to the genus *Escherichia*, such as *E. coli* VL334thrC$^+$ (EP 1172433). *E. coli* VL334 (VKPM B-1641) is an L-isoleucine and L-threonine auxotrophic strain having mutations in thrC and ilvA genes (U.S. Pat. No. 4,278,765). A wild-type allele of the thrC gene was transferred by the method of general transduction using a bacteriophage P1 grown on the wild-type *E. coli* strain K12 (VKPM B-7) cells. As a result, an L-isoleucine auxotrophic strain VL334thrC$^+$ (VKPM B-8961), which is able to produce L-glutamic acid, was obtained.

Examples of parent strains which can be used to derive the L-glutamic acid-producing bacteria include, but are not limited to, strains in which expression of one or more genes encoding an L-glutamic acid biosynthetic enzyme are enhanced. Examples of such genes include genes encoding glutamate dehydrogenase (gdhA), glutamine synthetase (glnA), glutamate synthetase (gltAB), isocitrate dehydrogenase (icdA), aconitate hydratase (acnA, acnB), citrate synthase (gltA), phosphoenolpyruvate carboxylase (ppc), pyruvate carboxylase (pyc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose bisphosphate aldolase (fbp), phosphofructokinase (pfkA, pfkB), and glucose phosphate isomerase (pgi).

Examples of strains modified so that expression of the citrate synthetase gene, the phosphoenolpyruvate carboxylase gene, and/or the glutamate dehydrogenase gene is/are enhanced include those disclosed in EP1078989A, EP955368A, and EP952221A.

Examples of parent strains which can be used to derive the L-glutamic acid-producing bacteria also include strains having decreased or eliminated activity of an enzyme that catalyzes synthesis of a compound other than L-glutamic acid by branching off from an L-glutamic acid biosynthesis pathway. Examples of such enzymes include isocitrate lyase (aceA), α-ketoglutarate dehydrogenase (sucA), phosphotransacetylase (pta), acetate kinase (ack), acetohydroxy acid synthase (ilvG), acetolactate synthase (ilvI), formate acetyltransferase (pfl), lactate dehydrogenase (ldh), and glutamate decarboxylase (gadAB). Bacteria belonging to the genus *Escherichia* deficient in α-ketoglutarate dehydrogenase activity or having a reduced α-ketoglutarate dehydrogenase activity and methods for obtaining them are described in U.S. Pat. Nos. 5,378,616 and 5,573,945. Specifically, these strains include the following:

*E. coli* W3110sucA::Km$^R$
*E. coli* AJ12624 (FERM BP-3853)
*E. coli* AJ12628 (FERM BP-3854)
*E. coli* AJ12949 (FERM BP-4881)

*E. coli* W3110sucA::Km$^R$ is a strain obtained by disrupting the α-ketoglutarate dehydrogenase gene (hereinafter referred to as "sucA gene") of *E. coli* W3110. This strain is completely deficient in α-ketoglutarate dehydrogenase.

Other examples of L-glutamic acid-producing bacterium include those which belong to the genus *Escherichia* and have resistance to an aspartic acid antimetabolite. These strains can also be deficient in α-ketoglutarate dehydrogenase activity and include, for example, *E. coli* AJ13199 (FERM BP-5807) (U.S. Pat. No. 5,908,768), FFRM P-12379, which additionally has a low L-glutamic acid decomposing ability (U.S. Pat. No. 5,393,671), AJ13138 (FERM BP-5565) (U.S. Pat. No. 6,110,714), and the like.

Examples of L-glutamic acid-producing bacteria include mutant strains belonging to the genus *Pantoea* which are deficient in α-ketoglutarate dehydrogenase activity or have decreased α-ketoglutarate dehydrogenase activity, and can be obtained as described above. Such strains include *Pantoea ananatis* AJ13356 (U.S. Pat. No. 6,331,419). *Pantoea ananatis* AJ13356 was deposited at the National Institute of Bioscience and Human-Technology, Agency of Industrial Science and Technology, Ministry of International Trade and Industry (currently, National Institute of Advanced Industrial Science and Technology, International Patent Organism Depositary, Central 6, 1-1, Higashi 1-Chome, Tsukuba-shi, Ibaraki-ken, 305-8566, Japan) on Feb. 19, 1998 under an accession number of FERM P-16645. It was then converted to an international deposit under the provisions of Budapest Treaty on Jan. 11, 1999 and received an accession number of FERM BP-6615. *Pantoea ananatis* AJ13356 is deficient in α-ketoglutarate dehydrogenase activity as a result of disruption of the αKGDH-E1 subunit gene (sucA). The above strain was identified as *Enterobacter agglomerans* when it was isolated and deposited as the *Enterobacter agglomerans* AJ13356. However, it was recently re-classified as *Pantoea ananatis* on the basis of nucleotide sequencing of 16S rRNA and so forth. Although AJ13356 was deposited at the aforementioned depository as *Enterobacter agglomerans*, for the purposes of this specification, they are described as *Pantoea ananatis*.

L-Phenylalanine-Producing Bacteria

Examples of parent strains which can be used to derive L-phenylalanine-producing bacteria include, but are not limited to, strains belonging to the genus *Escherichia*, such as *E. coli* AJ12739 (tyrA::Tn10, tyrR) (VKPM B-8197); *E. coli* HW1089 (ATCC 55371) harboring the mutant pheA34 gene (U.S. Pat. No. 5,354,672); *E. coli* MWEC100-b (KR8903681); *E. coli* NRRL B-12141, NRRL B-12145, NRRL B-12146 and NRRL B-12147 (U.S. Pat. No. 4,407,952). Also, as a parent strain, *E. coli* K-12 [W3110 (tyrA)/pPHAB (FERM BP-3566), *E. coli* K-12 [W3110 (tyrA)/pPHAD] (FERM BP-12659), *E. coli* K-12 [W3110 (tyrA)/pPHATerm] (FERM BP-12662) and *E. coli* K-12 [W3110 (tyrA)/pBR-aroG4, pACMAB] named as AJ 12604 (FERM BP-3579) may be used (EP 488-424 B1). Furthermore, L-phenylalanine producing bacteria belonging to the genus *Escherichia* with an enhanced activity of the protein encoded by the yedA gene or the yddG gene may also be used (U.S. patent applications 2003/0148473 A1 and 2003/0157667 A1).

L-Tryptophan-Producing Bacteria

Examples of parent strains which can be used to derive the L-tryptophan-producing bacteria include, but are not limited to, strains belonging to the genus *Escherichia*, such as *E. coli* JP4735/pMU3028 (DSM10122) and JP6015/pMU91 (DSM10123) deficient in the tryptophanyl-tRNA synthetase encoded by mutant trpS gene (U.S. Pat. No. 5,756,345); *E. coli* SV164 (pGH5) having a serA allele encoding phosphoglycerate dehydrogenase free from feedback inhibition by serine and a trpE allele encoding anthranilate synthase not subject to feedback inhibition by tryptophan (U.S. Pat. No. 6,180,373); *E. coli* AGX17 (pGX44) (NRRL B-12263) and AGX6 (pGX50)aroP (NRRL B-12264) deficient in the enzyme tryptophanase (U.S. Pat. No. 4,371,614); *E. coli* AGX17/pGX50, pACKG4-pps in which a phosphoenolpyruvate-producing ability is enhanced (WO9708333, U.S. Pat. No. 6,319,696), and the like. L-tryptophan-producing bacteria belonging to the genus *Escherichia* with an enhanced activity of the identified protein encoded by the yedA gene or the yddG gene may also be used (U.S. patent applications 2003/0148473 A1 and 2003/0157667 A1).

Examples of parent strains which can be used to derive the L-tryptophan-producing bacteria also include strains in which one or more activities of the enzymes selected from anthranilate synthase, phosphoglycerate dehydrogenase, and tryptophan synthase are enhanced. Anthranilate synthase and phosphoglycerate dehydrogenase are both subject to feedback inhibition by L-tryptophan and L-serine, so that a mutation desensitizing the feedback inhibition may be introduced into these enzymes. Specific examples of strains having such a mutation include a *E. coli* SV164 which harbors desensitized anthranilate synthase and a transformant strain obtained by introducing into the *E. coli* SV164 the plasmid pGH5 (WO 94/08031), which contains a mutant serA gene encoding feedback-desensitized phosphoglycerate dehydrogenase.

Examples of parent strains which can be used to derive the L-tryptophan-producing bacteria also include strains into which the tryptophan operon which contains a gene encoding desensitized anthranilate synthase has been introduced (JP 57-71397 A, JP 62-244382 A, U.S. Pat. No. 4,371,614). Moreover, L-tryptophan-producing ability may be imparted by enhancing expression of a gene which encodes tryptophan synthase, among tryptophan operons (trpBA). The tryptophan synthase consists of α and β subunits which are encoded by the trpA and trpB genes, respectively. In addition, L-tryptophan-producing ability may be improved by enhancing expression of the isocitrate lyase-malate synthase operon (WO2005/103275).

L-Proline-Producing Bacteria

Examples of parent strains which can be used to derive L-proline-producing bacteria include, but are not limited to, strains belonging to the genus *Escherichia*, such as *E. coli* 702ilvA (VKPM B-8012) which is deficient in the ilvA gene and is able to produce L-proline (EP 1172433). The bacterium may be improved by enhancing the expression of one or more genes involved in L-proline biosynthesis. Examples of such genes for L-proline producing bacteria which are preferred include the proB gene coding for glutamate kinase of which feedback inhibition by L-proline is desensitized (DE Patent 3127361). In addition, the bacterium may be improved by enhancing the expression of one or more genes coding for proteins excreting L-amino acid from bacterial cell. Such genes are exemplified by the b2682 and b2683 genes (ygaZH genes) (EP1239041 A2).

Examples of bacteria belonging to the genus *Escherichia*, which have an activity to produce L-proline include the following *E. coli* strains: NRRL B-12403 and NRRL B-12404 (GB Patent 2075056), VKPM B-8012 (Russian patent application 2000124295), plasmid mutants described in DE Patent 3127361, plasmid mutants described by Bloom F. R. et al (The 15$^{th}$ Miami winter symposium, 1983, p. 34), and the like.

L-Arginine-Producing Bacteria

Examples of parent strains which can be used to derive L-arginine-producing bacteria include, but are not limited to, strains belonging to the genus *Escherichia*, such as *E. coli* strain 237 (VKPM B-7925) (U.S. Patent Application 2002/058315 A1) and its derivative strains harboring mutant N-acetylglutamate synthase (Russian Patent Application No. 2001112869), *E. coli* strain 382 (VKPM B-7926) (EP1170358A1), an arginine-producing strain into which argA gene encoding N-acetylglutamate synthetase is introduced therein (EP1170361 A1), and the like.

Examples of parent strains which can be used to derive L-arginine producing bacteria also include strains in which expression of one or more genes encoding an L-arginine biosynthetic enzyme are enhanced. Examples of such genes include genes encoding N-acetylglutamyl phosphate reductase (argC), ornithine acetyl transferase (argJ), N-acetylglutamate kinase (argB), acetylornithine transaminase (argD), ornithine carbamoyl transferase (argF), argininosuccinic acid synthetase (argG), argininosuccinic acid lyase (argH), and carbamoyl phosphate synthetase (carAB).

L-Valine-Producing Bacteria

Example of parent strains which can be used to derive L-valine-producing bacteria include, but are not limited to, strains which have been modified to overexpress the ilvGMEDA operon (U.S. Pat. No. 5,998,178). It is desirable to remove the region of the ilvGMEDA operon which is required for attenuation so that expression of the operon is not attenuated by the L-valine that is produced. Furthermore, the ilvA gene in the operon is desirably disrupted so that threonine deaminase activity is decreased.

Examples of parent strains which can be used to derive L-valine-producing bacteria also include mutants having a mutation of amino-acyl t-RNA synthetase (U.S. Pat. No. 5,658,766). For example, *E. coli* VL1970, which has a mutation in the ileS gene encoding isoleucine tRNA synthetase, can be used. *E. coli* VL1970 has been deposited in the Russian National Collection of Industrial Microorganisms (VKPM) (Russia, 117545 Moscow, 1$^{st}$ Dorozhny Proezd, 1) on Jun. 24, 1988 under accession number VKPM B-4411.

Furthermore, mutants requiring lipoic acid for growth and/or lacking H$^+$-ATPase can also be used as parent strains (WO96/06926).

L-Isoleucine-Producing Bacteria

Examples of parent strains which can be used to derive L-isoleucine producing bacteria include, but are not limited to, mutants having resistance to 6-dimethylaminopurine (JP 5-304969 A), mutants having resistance to an isoleucine analogue such as thiaisoleucine and isoleucine hydroxamate, and mutants additionally having resistance to DL-ethionine and/or arginine hydroxamate (JP 5-130882 A). In addition, recombinant strains transformed with genes encoding proteins involved in L-isoleucine biosynthesis, such as threonine deaminase and acetohydroxate synthase, can also be used as parent strains (JP 2-458 A, FR 0356739, and U.S. Pat. No. 5,998,178).

3. Method for Producing the Useful Metabolite of the Present Invention

The method for producing a useful metabolite includes cultivating the bacterium in a culture medium to produce and excrete the useful metabolite into the medium, and collecting the useful metabolite from the medium.

In the present invention, the cultivation, collection, and purification of an L-amino acid from the medium and the like may be performed in a manner similar to conventional fermentation methods wherein a metabolite is produced using a bacterium.

The chosen medium may be either a synthetic or natural medium, so long as it includes a carbon source, a nitrogen source, minerals, and if necessary, appropriate amounts of nutrients which the bacterium requires for growth. The carbon source may include various carbohydrates such as glucose and sucrose, and various organic acids. Depending on the mode of assimilation of the chosen microorganism, alcohol, including ethanol and glycerol, may be used. As the nitrogen source, various ammonium salts such as ammonia and ammonium sulfate, other nitrogen compounds such as amines, a natural nitrogen source such as peptone, soybean-hydrolysate, and digested fermentative microorganism can be used. As minerals, potassium monophosphate, magnesium sulfate, sodium chloride, ferrous sulfate, manganese sulfate, calcium chloride, and the like can be used. As vitamins, thiamine, yeast extract, and the like, can be used.

The cultivation is preferably performed under aerobic conditions, such as a shaking culture, and a stirring culture with aeration, at a temperature of 20 to 40° C., preferably 30 to 38° C. The pH of the culture is usually between 5 and 9, preferably between 6.5 and 7.2. The pH of the culture can be adjusted with ammonia, calcium carbonate, various acids, various bases, and buffers. Usually, a 1 to 5-day cultivation leads to accumulation of the target L-amino acid in the liquid medium.

After cultivation, solids such as cells can be removed from the liquid medium by centrifugation or membrane filtration, and then the L-amino acid can be collected and purified by ion-exchange, concentration, and/or crystallization methods.

4. A Method for the Quantitative Analysis of Gene Expression

Another method is a method for quantitative analysis of gene expression including:
constructing an expression system having the gene for which expression is to be measured translationally coupled with a marker gene by the method described above;
expressing the translationally coupled genes; and
measuring the activity of the protein encoded by the marker gene.

Examples of marker genes include the lacZ gene coding for β-galactosidase, any gene coding for a protein having measurable enzymatic activity, or the gfp (rfp, bfp, yfp) gene coding for fluorescent protein. β-galactosidase activity is measured according to a routine method (Miller, 1972). Translation of the marker gene depends on the translation of the gene to which it is coupled, and the dependence is linear.

EXAMPLES

The present invention will be more concretely explained below with reference to the following non-limiting Examples.

Example 1

Construction of a Strain Containing the Translationally Coupled aroG4-serA5 Operon 1. Construction of Plasmid pMDV3-$P_{tac-ideal}$.

The plasmid pMDV3-$P_{tac-ideal}$ was constructed on the basis of the integrative plasmid pMDV3 (Zimenkov D. et al., Biotechnology in Russia, 6, 1-22 (2004)). Two DNA fragments were cloned into pMDV3. The first fragment was the DNA fragment BglII-XbaI of plasmid pMW118-$P_{tac-ideal}$-lacZ-ter_rrnB (Mashko S. et. al., Biotechnology in Russia, 5, 3-20 (2001)), containing promoter $P_{tac-ideal}$ ($O_{lac-ideal}$-$P_{tac}$/$O_{lac}$). The second fragment was the DNA fragment XbaI-EcoRI of polylinker from plasmid pMW118 (GenBank/EMBL accession number AB005475). The obtained plasmid pMDV3-$P_{tac-ideal}$ was then used as a vector to clone the aroG4 gene.

2. Construction of Plasmid pMDV3-$P_{tac-ideal}$-aroG4.

The DNA fragment containing aroG4 was obtained by PCR using plasmid pAROG4 (Kikuchi Y. et. al., Appl. And Env. Microb., 761-2 (1997)) as a template and primers P1 (SEQ ID NO: 1) and P2 (SEQ ID NO: 2), which contain the recognition sites for the XbaI and SmaI endonucleases respectively. Primer P1 additionally contains an artificial ribosome binding site (RBS). Conditions for PCR were as follows: denaturation step for 3 min at 95° C.; profile for two first cycles: 1 min at 95° C., 30 sec at 50° C., 40 sec at 72° C.; profile for the last 25 cycles: 30 sec at 95° C., 30 sec at 54° C., 40 sec at 72° C.; final step: 5 min at 72° C. The PCR product was purified in an agarose gel, treated with endonucleases XbaI and SmaI and cloned into the plasmid pMDV3-$P_{tac-ideal}$. The resulting plasmid pMDV3-$P_{tac-ideal}$-aroG4 was used to transform E. coli cells AB3257 (aroF, aroG, aroH) (Kikuchi Y. et. al., Appl. And Env. Microb., 761-2 (1997); Wallace, B. J. and Pittard J., J. Bacteriol., 99(3): 707-712 (1969)), which are of the Aro⁻-phenotype. The plasmid containing a functionally active copy of aroG4 was selected using genetic complementation. Transformants harboring the plasmid containing a functionally active copy of aroG4 could grow on minimal medium containing glucose.

3. Construction of Plasmid pMDV3-$P_{tac-ideal}$-aroG4-serA5.

The plasmid pMDV3-$P_{tac-ideal}$-aroG4 was used as a vector to clone the structural part of the serA5 gene. The amplified DNA fragment containing serA5 was obtained by PCR using the plasmid pGH5 (U.S. Pat. No. 6,180,373) as a template and primers P3 (SEQ ID NO: 3) and P4 (SEQ ID NO: 4). This amplified fragment had the recognition site for SmaI endonuclease in the 5'-region of serA5 gene and the recognition sites for SalL SphI, SacI endonucleases in the 3'-region of serA5 gene. This DNA fragment was cloned into plasmid pMDV3-$P_{tac-ideal}$-aroG4 by the recognition sites for SmaI and SacI endonucleases. The resulting plasmid pMDV3-$P_{tac-ideal}$-aroG4-serA5 contained operon $P_{tac-ideal}$→aroG4-serA5. The nucleotide sequence of the operon $P_{tac-ideal}$→aroG4-serA5 is shown in SEQ ID NO: 34. The position of the genes in the operon is as follows: $P_{tac-ideal}$ (1 to 116), aroG4 (133 to 1185), and serA5 (1209 to 2438). In aroG4, the L-proline at position 150 in the wild-type deoxyarabino-heptulosonate phosphate synthase (SEQ ID NO: 20) is replaced by L-leucine. In serA5, the tyrosine residue at position 410 in the wild-type phosphoglycerate dehydrogenase (SEQ ID NO: 18) is deleted.

4. Mu-Dependent Integration of Cassette pMDV3-aroG4-serA5 into Chromosome of E. coli using the aroG4 Gene as a Selectable Marker.

The plasmid pMDV3-aroG4-serA5 was integrated into the chromosome of *E. coli* strain AB3257 (aroF, aroG, aroH) (Kikuchi Y. et. al., Appl. And Env. Microb., 761-2 (1997)), having Aro⁻-phenotype. The *E. coli* AB3257 strain was transformed with helper plasmid pMH10 (Zimenkov D. et al., Biotechnology in Russia, 6, 1-22 (2004)), and transformed clones were selected on LB agar containing Tc (10 µg/ml) at 28° C. Then, the transformed clones were used as recipient strains for integration of plasmid pMDV3-aroG4-serA5. An overnight culture of AB3257-[pMH10] was diluted 100 times and grown in LB medium containing Tc (10 µg/ml) at 28° C. until $OD_{600}$~0.6. Transformation with the integrative plasmid was performed as described in Sambrook, J., Fritsch, E. F., and Maniatis, T., "Molecular Cloning: A Laboratory Manual, Second Edition", Cold Spring Harbor Laboratory Press (1989). After heat shock at 42° C., cells were incubated at 44° C. for 20 min, then at 37° C. for 40 min. Transformed clones were selected at 37° C. on M9-agar containing glucose, Tc (10 µg/ml), Ap (100 µg/ml). Selected clones were transferred to the medium containing Ap (100 µg/ml) and cultivated at 37° C. $Tc^S$ clones without plasmid pMH10, were selected. Selected clones were incubated in LB broth at 42° C. without aeration to be cured of the integrative plasmid pMDV3-aroG4-serA5. The presence of the integrated expression cassette in the chromosome of Aro⁺, Aps clones was confirmed using PCR.

The positions of integration on the chromosome were determined as described in (Zimenkov D. et al., Biotechnology in Russia, 6, 3-22 (2004)). Clones with the expression cassette containing the operon $P_{tac-ideal}$-aroG4-serA5 integrated into the chromosome at the position 2.933.542 was used for further development.

5. Integration of the cat Gene Downstream of the serA5 Gene of the Artificial Cassette Carrying Operon $P_{tac-ideal}$→aroG4-serA5.

An excisible Cm resistance marker (λattL-cat-λattR) was introduced into the integrated cassette between the serA5 gene and adjacent to the transcription terminators of phage fd (2Tfd) using Red-driven integration (Datsenko, K. A. and Wanner, B. L., Proc. Natl. Acad. Sci. USA, 97, 12, p 6640-6645 (2000)). A DNA fragment containing the Cm resistance marker was obtained by PCR using the plasmid pMW118-(λattL-$Cm^R$-λattR) (WO 05/010175) as a template and primers P30 (SEQ ID NO: 30) and P31 (SEQ ID NO: 31). The integration of the Cm resistance gene into the $P_{tac-ideal}$→aroG4-serA5 operon was verified by PCR. Locus-specific confirmation primers P32 (SEQ ID NO: 32) and P33 (SEQ ID NO: 33) were used in PCR for verification. The PCR product with the λattL-cat-λattR integrated into the desired position was 2019 bp in length. The resulting strain was named AB3257 [$P_{tac-ideal}$-aroG4-serA5-cat]. This strain was used as the donor of the cassette with the cat gene for construction of the control BW25113 [$P_{tac-ideal}$→aroG4-serA5] and SV164 [$P_{tac-ideal}$→aroG4-serA5] strains (see below).

To obtain the parental strain having the cassette with the uncoupled aroG4-serA5 genes used for further construction of the strain with translationally coupled aroG4-serA5 genes, the Cm resistance gene (cat gene) located downstream of the serA5 gene was eliminated from the chromosome of AB3257 [$P_{tac-ideal}$-aroG4-serA5-cat] using the int-xis system (WO 05/010175). For that purpose, the AB3257 [$P_{tac-ideal}$-aroG4-serA5-cat] strain was transformed with plasmid pMWts-Int/Xis (WO 05/010175). Transformant clones were selected on LB-medium containing 100 µg/ml of ampicillin. Plates were incubated overnight at 30° C. Transformant clones were cured from the cat gene by spreading the separate colonies at 37° C. (at that temperature repressor CIts is partially inactivated and transcription of the int/xis genes is derepressed) followed by selection of $Cm^S Ap^R$ variants. To eliminate the pMWts-Int/Xis plasmid, selected variants were disseminated to separate colonies, and then cultivated at 37° C. followed by selection of $Ap^S$ clones. The resulting strain was named AB3257 [$P_{tac-ideal}$-aroG4-serA5].

6. Construction of Cassettes for Translational Coupling of Genes.

A DNA fragment containing the λattL-cat-λattR sequence flanked by regions of the rplC-rplD and trpE-trpD genes and regions homologous to the aroG4 and serA5 genes was amplified using two rounds of PCR as follows.

The plasmid pMW118-(λattL-$Cm^R$-λattR) was used as the template and P5 (SEQ ID NO: 5) and P6 (SEQ ID NO: 6) were used as primers for the first round of PCR. The 5'-end of primer P5 contains the region located between the translationally coupled rplC-rplD genes. The 5'-end of primer P6 contains the region containing the overlapping stop-codon and start-codon of the translationally coupled trpE and trpD genes, respectively. The PCR product was purified in an agarose gel and amplified using the second round of PCR with primers P7 (SEQ ID NO: 7) and P8 (SEQ ID NO: 8). The 5'-end of primers P7 and P8 contains the 38 nucleotide and 36 nucleotide regions which are homologous to the 3'-end of the aroG4 gene and the 5'-end of serA5 gene, respectively. Integration of the relevant fragment into the operon $P_{tac-ideal}$→aroG4-serA5 in the *E. coli* strain AB3257 was accomplished using Red-driven integration (Datsenko, K. A. and Wanner, B. L., Proc. Natl. Acad. Sci. USA, 97, 12, p 6640-6645 (2000)). Correspondence of the resulting structure in the chromosome to the targeted one was confirmed using PCR with the confirmation primers P9 (SEQ ID NO: 9) and P10 (SEQ ID NO: 10). The PCR product obtained in the reaction with the cells containing the λattL-cat-λattR sequence in the analyzed region was 1960 bp in length. The PCR product obtained in the reaction using the parental cells was 302 bp in length. After elimination of the Cm resistance marker using the int-xis system, the PCR product was 354 bp in length. The strain containing the rplC'D-attR-cat-attL-trpE'D cassette integrated into the operon $P_{tac-ideal}$→aroG4-serA5 was named AB3257 [$P_{tac-ideal}$→aroG4-(rpl'D-attR-cat-attL-trpE')-serA5].

Translational coupling of the aroG4 and serA5 genes using other regions, such as lgt-thyA, trpCB, trpBA, thrBC, and hisHA, can be performed by the same technique as described above. Primers which can be used in the above technique and the constructs are summarized in Table 1. The PCR product obtained in the reaction with the cells containing the λattL-cat-λattR cassette as a template in PCR with confirmation primers P9 (SEQ ID NO: 9) and P10 (SEQ ID NO: 10) is about 1960 bp in length. The PCR product obtained in the reaction with the parental cells as a template is about 300 bp in length. After elimination of the Cm resistance marker using the int-xis system, the PCR product obtained in the reaction with the cells as a template is about 350 bp in length.

Translational coupling of any other adjacent genes can be performed using regions providing translational coupling as described above. For that purpose, primers used in the first round of PCR are universal. In the second round of PCR, primers should contain regions homologous the 3'-end of the first gene and 5-end of the second gene necessary for integration, and regions homologous to the corresponding regions to effectively translationally couple the first and second genes, respectively.

Thus, translational coupling of the adjacent zwf and edd genes located next to each other in the zwf-edd-eda operon on the chromosome of *E. coli* can be performed by the same techniques as described above. Primers useful in the above techniques and the constructs are also summarized in Table 1. The PCR product obtained in the reaction with the cells containing the λattL-cat-λattR cassette as a template in PCR with confirmation primers P21 (SEQ ID NO: 21) and P22 (SEQ ID NO: 22) is about 1880 bp in length. The PCR product obtained in the reaction with the parental cells as a template is about 440 bp in length. After elimination of the Cm resistance marker using the int-xis system, the PCR product obtained in the reaction with the cells as a template is about 280 bp in length.

Any of above cassettes can be transferred into a strain of interest by, for example, P1 transduction. Selection of the necessary strain can be performed using resistance to chloramphenicol.

In all cases, adjacent genes containing one of the above cassettes became translationally coupled only after excision of the chloramphenicol marker encoded by the cat gene using int-xis system.

Example 2

Expression of the Genes aroG4 and serA5 on the Translationally Coupled Operon

To test the effect of translational coupling of the aroG4-serA5 operon on the amounts of the AroG and SerA proteins produced, two strains, BW25113 [$P_{tac-ideal}$→aroG4-(rplD'-attB-trpE')-serA5] and BW25113 [$P_{tac-ideal}$→aroG4-serA5], were constructed.

DNA fragments from the chromosome of the above-described E. coli strain AB3257 [$P_{tac-ideal}$→aroG4-(rplD-attR-cat-attL-trpE')-serA5] were transferred to the E. coli strain BW25113 (lacI$^q$, rrnB$_{T14}$, ΔlacZ$_{WJ16}$, hsdR514, Δara-BAD$_{AH33}$, ΔrhaBAD$_{LD78}$) by P1 transduction to obtain the strain BW25113 [$P_{tac-ideal}$→aroG4-(rplD-attR-cat-attL-trpE')-serA5].

Furthermore, the Cm resistance gene (cat gene) was eliminated from the chromosome of the BW25113 [$P_{tac-ideal}$→aroG4-(rplD-attR-cat-attL-trpE')-serA5] strain using the int-xis system (WO 05/010175) as described above (see Example 1, part 5). The obtained strain was named BW25113 [$P_{tac-ideal}$→aroG4-(rplD'-attB-trpE')-serA5]. The nucleotide sequence of the translationally coupled operon P$_{tac-ideal}$→aroG4-(rplD'-attB-trpE')-serA5 is shown in SEQ ID NO: 35.

To test the effect of translational coupling of aroG4-serA5 on the amounts of the AroG and SerA proteins produced, the strain BW25113 [$P_{tac-ideal}$→aroG4-(rplD'-attB-trpE')-serA5] was compared to the strain BW25113 [$P_{tac-ideal}$→aroG4-serA5]. DNA fragments from the chromosome of the above-described E. coli strain AB3257 [$P_{tac-ideal}$→aroG4-serA5-cat] were transferred to the E. coli strain BW25113 by P1 transduction to obtain the strain BW25113 [$P_{tac-ideal}$→aroG4-serA5-cat]. E. coli strain BW25113 containing the recombinant plasmid pKD46 can be obtained from the E. coli Genetic Stock Center, Yale University, New Haven, USA, the accession number of which is CGSC7630. The strain BW25113/pKD46 was cured of the thermosensitive plasmid pKD46 by culturing at 37° C. the resulting strain BW25113. The Cm resistance gene (cat gene) was eliminated from the chromosome BW25113 [$P_{tac-ideal}$→aroG4-serA5-cat] strain using the int-xis system as described above (see Example 1, part 5). The obtained strain was named BW25113-[$P_{tac-ideal}$→aroG4-serA5].

To estimate the change in the biosynthesis of the SerA5 protein in the strains BW25113 [$P_{tac-ideal}$→aroG4-(rplD'-attB-trpE')-serA5] and BW25113 [$P_{tac-ideal}$→aroG4-serA5], proteome research was carried out as described in Rabilloud T. Proteome research: Two dimensional gel electrophoresis and identification methods (principals and methods). Springer, N.Y. (2000). Proteome research included some of the following steps:

1) Extraction of soluble proteins from the E. coli cells was carried out as recommended by Amersham Biosciences (USA) (2-D Electrophoresis Principles and Methods. Amersham Biosciences AB (2001)) and by Rabilloud T. Proteome research: Two dimensional gel electrophoresis and identification methods (principals and methods). Springer, N.Y. (2000). Concentration of protein in samples was measured using Bradford reagent, the amount of protein was estimated spectrophotometrically at 595 nm.

2) Gel-rehydration and isoelectrofocusing were carried out on platform Ettan IPGphor ("Amersham", USA) at 20° C. using PAAG (4%)-stripes (IPG drystrip pH 4-7, "Amersham", USA) as recommended by the manufacturer.

3) Vertical protein gel-electrophoresis was performed in 12% PAAG in the presence of 0.1% SDS as described in Laemmli V. K. Cleavage of structural proteins during the assembly of the head of bacteriophage T4. Nature. 227, 680-685 (1970), Rabilloud T. Proteome research: Two dimensional gel electrophoresis and identification methods (principals and methods). Springer, N.Y. (2000), and 2-D Electrophoresis Principles and Methods. Amersham Biosciences AB (2001). Camera Ettan DALTsix, current supply EPS-601 and thermostatic circulator MultiTemp III ("Amersham", USA) were used for electrophoresis. Gels were stained with Comassie G-250 as described in Merril, C. R. Gel-staining techniques. Method Enzymol., 182, 477 (1990).

4) Computer analysis of the gels stained with Comassie G-250 was performed on PowerLook 1000 ("Umax", USA) using the program MagicScan with preset resolving capacity 200 and 300 dpi for each sample. The obtained gels' pictures were treated using program Melanie 4. AroG and SerA proteins' zones were detected using known values of corresponding isoelectric points and molecular weights and were cut out of the gels for mass-spectrometric analysis.

5) Mass-spectrometric analysis of possible AroG and SerA. Identification of samples was performed using MALDI-TOF (matrix-assisted laser desorption/ionization time-of-flight) mass-spectrometric analysis of lysate of these proteins after tryptic cleavage using standard protocols. Mass-spectra of lysate of the proteins were obtained using apparatus REFLEX III ("Bruker Daltonics", Germany). Identification of spectra of proteins was performed using the program Mascot with set-up: data-base is NCBInr; protease is trypsin; quantity of allowable absence of tryptic cleavage is 1; possible modifications are oxidation of methionine and modification of cysteine by acrylamide; measure of inaccuracy at detection of the peptide's mass is 100 ppm (parts per million).

Cells at exponential growth phase, that grown on LB medium supplemented with IPTG (specific inductor of integrated operon), were used for proteome research. The results of the proteome research are shown in Table 2. Rates (%) of intensity of spots corresponding to AroG and SerA proteins of total proteins' intensity were normalized for molecular weights of AroG and SerA proteins, 37852 Da and 44015 Da, respectively. As follows from Table 2, the proportion of synthesis of AroG and SerA proteins (AroG/SerA) is different in the strains BW25113 [$P_{tac-ideal}$→aroG4-(rplD'-attB-trpE')-serA5] and BW25113 [$P_{tac-ideal}$→aroG4-serA5]. Translational coupling results in a decrease of the difference between the expression levels of the genes aroG4 and serA5.

Example 3

Production of L-Tryptophan by E. Coli Strain SV164 [$P_{tac\text{-}ideal}$→aroG4-(rplD'-attB-trpE')-serA5]

To test the effect of translational coupling of the aroG4-serA5 operon on L-tryptophan production, a DNA fragment from the chromosome of the above-described E. coli strain AB3257 [$P_{tac\text{-}ideal}$→aroG4-(rpl'D-attR-cat-attL-trpE')-serA5] was transferred to the tryptophan-producing E. coli strain SV164 by P1 transduction to obtain the strain SV164 [$P_{tac\text{-}ideal}$→aroG4-(rpl'D-attR-cat-attL-trpE')-serA5]. The strain SV164 has the trpE allele encoding an anthranilate synthase which is not subject to feedback inhibition by tryptophan.

The Cm resistance gene (cat gene) was eliminated from the chromosome of the SV164 [$P_{tac\text{-}ideal}$→aroG4-(rpl'D-attR-cat-attL-trpE')-serA5] strain using the int-xis system as described above (see Example 1, part 5). The obtained strain was named SV164-[$P_{tac\text{-}ideal}$→aroG4-(rplD'-attB-trpE')-serA5].

To test the effect of translational coupling of the aroG4-serA5 operon on L-tryptophan production, the strain SV164 [$P_{tac\text{-}ideal}$→aroG4-(rplD'-attB-trpE')-serA5] was compared to the strain SV164 [$P_{tac\text{-}ideal}$→aroG4-serA5]. DNA fragments from the chromosome of the above-described E. coli strain AB3257 [$P_{tac\text{-}ideal}$→aroG4-serA5-cat] were transferred to the tryptophan-producing E. coli strain SV164 by P1 transduction to obtain the strain SV164-[$P_{tac\text{-}ideal}$→aroG4-serA5-cat]. The Cm resistance gene (cat gene) was eliminated from the chromosome SV164 [$P_{tac\text{-}ideal}$-aroG4-serA5-cat] strain using the int-xis system as described above (see Example 1, part 5) The obtained strain was named SV164 [$P_{tac\text{-}ideal}$→aroG4-serA5].

Three strains, SV164, SV164 [$P_{tac\text{-}ideal}$→aroG4-serA5], and SV164 [$P_{tac\text{-}ideal}$→aroG4-(rplD'-attB-trpE')-serA5], were each cultivated with shaking at 32° C. for 18 hours in 3 ml of nutrient broth. The obtained cultures (0.3 ml each) were inoculated into 3 ml of a fermentation medium in 20×200-mm test tubes, and cultivated at 32° C. for 72 hours with a rotary shaker at 250 rpm. After cultivation, the amount of tryptophan which is present in the medium was determined by TLC. The 10×15-cm TLC plates coated with 0.11-mm layers of Sorbfil silica gel containing no fluorescent indicator (Stock Company Sorbpolymer, Krasnodar, Russia) were used. The Sorbfil plates were developed with a mobile phase consisting of propan-2-ol: ethylacetate: 25% aqueous ammonia:water=40:40:7:16 (v/v). A solution of ninhydrin (2%) in acetone was used as a visualizing reagent.

The results of three independent test tube fermentations are shown in Table 4. As follows from Table 4, SV164 [$P_{tac\text{-}ideal}$→aroG4-(rplD'-attB-trpE')-serA5] produced a higher amount of L-tryptophan, as compared with both SV164 [$P_{tac\text{-}ideal}$→aroG4-(CmR)-serA5] and SV164.

The fermentation medium components are listed in Table 3, but should be sterilized in separate groups (A, B, C, D, E, F, G and H), as shown, to avoid adverse interactions during sterilization.

Example 4

Construction of Strains Containing Operons with Translationally Coupled aroE-aroC Genes and aroD-aroE-aroC Genes 1. Construction the Strain with $P_{tac\text{-}10000}$→aroD-aroE-aroC Operon.

The starting strain used to contruct the E. coli strain containing $P_{tac\text{-}10000}$→aroD-aroE-aroC was the E. coli strain MG1655 containing expression cassette cat-$P_{tac\text{-}10000}$→aroD-aroE-aroC (SEQ ID NO: 60) integrated at the point 3.930.092 of the chromosome. The detailed description of the attR-cat-attL-$P_{tac\text{-}10000}$→aroDEC cassette is shown in the Table 5. The chloramphenicol resistance gene (cat gene) was excised from the chromosome of strain MG1655 [cat-$P_{tac\text{-}10000}$→aroD-aroE-aroC] using the int-xis system as described above (Example 1, part 5). The obtained strain was named MG1655 [$P_{tac\text{-}10000}$→aroD-aroE-aroC].

2. Construction of Cassettes for the Translational Coupling of the Genes.

A DNA fragment containing the λattL-cat-λattR sequence flanked by regions of the rplC-rplD and trpE-trpD genes and regions homologous to the aroE and aroC genes was amplified using two rounds of PCR as follows.

The plasmid pMW118-(λattL-Cm$^R$-λattR) was used as the template and P5 (SEQ ID NO: 5) and P6 (SEQ ID NO: 6) were used as primers for the first round of PCR. The 5'-end of primer P5 contains the region located between the translationally coupled rplC-rplD genes. The 5'-end of primer P6 contains the region containing the overlapping stop-codon and start-codon of the translationally coupled trpE and trpD genes, respectively. The PCR product was purified in an agarose gel and amplified using the second round of PCR with primers P34 (SEQ ID NO: 61) and P35 (SEQ ID NO: 62). The 5'-end of primer P34 contains the 36 nucleotide regions which are homologous to the 3'-end of the aroE gene and two nucleotides substituting native TGA stop-codon of aroE gene by TAA stop-codon. The 5'-end of primer P35 contains the 36 nucleotide regions which are homologous to the 5'-end of the aroC gene.

Integration of the relevant fragment into the operon $P_{tac\text{-}10000}$→aroD-aroE-aroC in the E. coli strain MG1655 was accomplished using Red-driven integration (Datsenko, K. A. and Wanner, B. L., Proc. Natl. Acad. Sci. USA, 97, 12, p 6640-6645 (2000)). Correspondence of resulting structure in the chromosome to the targeted one was confirmed using PCR with the confirmation primers P36 (SEQ ID NO: 63) and P37 (SEQ ID NO: 64). The PCR product obtained in the reaction with the cells containing the λattL-cat-λattR sequence in the analyzed region was 2036 bp in length. The PCR product obtained in the reaction using the parental cells was 388 bp in length. After elimination of Cm resistance marker using the int-xis system, the PCR product was 430 bp in length. The strain containing rplC'D-attR-cat-attL-trpE'D cassette integrated into operon $P_{tac\text{-}10000}$→aroD-aroE-aroC was named MG1655 [$P_{tac\text{-}10000}$→aroD-aroE-(rpl'D-attB-trpE')-aroC].

E. coli strain MG1655 [$P_{tac\text{-}10000}$→aroD-(rpl'D-attR-cat-attL-trpE')-aroE-(rpl'D-attB-trpE')-aroC] was obtained in a similar way.

A DNA fragment containing the λattL-cat-λattR sequence flanked by regions of the rplC-rplD and trpE-trpD genes and regions homologous to the aroD and aroE genes was amplified using two rounds of PCR as follows.

The plasmid pMW118-(λattL-Cm$^R$-λattR) was used as the template and P38 (SEQ ID NO: 65) and P39 (SEQ ID NO: 66)

were used as primers for the first round of PCR. The 5'-end of primer P38 contains the region located between the translationally coupled rplC-rplD genes. The 5'-end of primer P39 contains the region containing the overlapping stop-codon and start-codon of the translationally coupled trpE and trpD genes, respectively. The PCR product was purified in an agarose gel and amplified using the second round of PCR with primers P40 (SEQ ID NO: 67) and P41 (SEQ ID NO: 68). The 5'-ends of primers P40 and P41 contain the 38 and 36 nucleotide regions which are homologous to the 3'-end of the aroD gene and 5'-end of the aroE gene, respectively.

Integration of the relevant fragment into the operon $P_{tac-10000}$→aroD-aroE-(rpl'D-attB-trpE')-aroC in the *E. coli* strain MG1655 [$P_{tac-10000}$→aroD-aroE-(rpl'D-attB-trpE')-aroC] was accomplished using Red-driven integration (Datsenko, K. A. and Wanner, B. L., Proc. Natl. Acad. Sci. USA, 97, 12, p 6640-6645 (2000)). Correspondence of the resulting structure in the chromosome to the targeted one was confirmed using PCR with the confirmation primers P42 (SEQ ID NO: 69) and P43 (SEQ ID NO: 70). The PCR product obtained in the reaction with the cells containing the λattL-cat-λattR sequence in the analyzed region was 1864 bp in length. The PCR product obtained in the reaction using the parental cells was 205 bp in length. After elimination of Cm resistance marker using the int-xis system, the PCR product was 258 bp in length. The strain containing rplC'D-attR-cat-attL-trpE'D cassette integrated into operon $P_{tac-10000}$→aroD-aroE-(rpl'D-attB-trpE')-aroC between aroD and aroE genes was named MG1655 [$P_{tac-10000}$→aroD-(rpl'D-attR-cat-attL-trpE')-aroE-(rpl'D-attB-trpE')-aroC].

As it was mentioned above, primers P5 and P38 contain the region located between the translationally coupled rplC-rplD genes, and primers P6 and P39 contain the region containing the overlapping stop-codon and start-codon of the translationally coupled trpE and trpD genes, respectively. Downstream of said region, each primer contains six nucleotides which are varied to avoid integration of the DNA fragment into the location created during the previous procedure of translational coupling. It allows the acquisition of the DNA fragment with six various nucleotides in the position after the initiation codon in the first intercistronic region and the position before the SD-sequence in the second intercistronic region of the DNA fragment. These regions are depicted in FIG. 2 in the white boxes.

Any of above cassettes can be transferred into a strain of interest by, for example, P1 transduction. Selection of the necessary strain can be performed using resistance to chloramphenicol.

In all cases, adjacent genes containing one of the above cassettes became translationally coupled only after excision of the chloramphenicol marker encoded by the cat gene using the int-xis system.

Example 5

Expression of the aroD, aroE, and aroC Genes in the Translationally Coupled Operon To test the effect of translational coupling of the aroD-aroE-aroC operon on the amounts of the AroD, AroE and AroC proteins, three strains, BW25113 [$P_{tac-10000}$→aroD-aroE-aroC], BW25113 [$P_{tac-10000}$→aroD-aroE-(rpl'D-attB-trpE')-aroC] and [$P_{tac-10000}$→aroD-(rpl'D-attB-trpE')-aroE-(rpl'D-attB-trpE')-aroC], were constructed.

DNA fragments from the chromosome of the above-described *E. coli* strains MG1655 [$P_{tac-10000}$→aroD-aroE-(rpl'D-attR-cat-attL-trpE')-aroC] and MG1655 [$P_{tac-10000}$→aroD-(rpl'D-attR-cat-attL-trpE')-aroE-(rpl'D-attB-trpE')-aroC] were transferred to the *E. coli* strain BW25113 (lacI$^q$, rrnB$_{T14}$, ΔlacZ$_{WJ16}$, hsdR514, ΔaraBAD$_{AH33}$, ΔrhaBAD$_{LD78}$) by P1 transduction to obtain the strains BW25113 [$P_{tac-10000}$→aroD-aroE-(rpl'D-attR-cat-attL-trpE')-aroC] and BW25113 [$P_{tac-10000}$→aroD-(rpl'D-attR-cat-attL-trpE')-aroE-(rpl'D-attB-trpE')-aroC], respectively.

Furthermore, the Cm resistance gene (cat gene) was eliminated from the chromosome of the strains BW25113 [$P_{tac-10000}$→aroD-aroE-(rpl'D-attR-cat-attL-trpE')-aroC] and BW25113 [$P_{tac-10000}$→aroD-(rpl'D-attR-cat-attL-trpE')-aroE-(rpl'D-attB-trpE')-aroC] using the int-xis system (WO 05/010175) as described above (see Example 1, part 5). The obtained strains were named BW25113 [$P_{tac-10000}$→aroD-aroE-(rpl'D-attB-trpE')-aroC] and [$P_{tac-10000}$→aroD-(rpl'D-attB-trpE')-aroE-(rpl'D-attB-trpE')-aroC], respectively. The nucleotide sequences of the region between aroE and aroC genes within the translationally coupled operons $P_{tac-10000}$→aroD-aroE-(rpl'D-attB-trpE')-aroC and $P_{tac-10000}$→aroD-(rpl'D-attB-trpE')-aroE-(rpl'D-attB-trpE')-aroC $P_{tac-ideal}$→aroG4-(rplD'-attB-trpE')-serA5 were confirmed by sequence analysis. The sequence is shown in SEQ ID NO: 71. The nucleotide sequence of the region between aroD and aroE genes within the translationally coupled operon $P_{tac-10000}$→aroD-(rpl'D-attB-trpE')-aroE-(rpl'D-attB-trpE')-aroC is shown in SEQ ID NO: 72.

To test the effect of translational coupling of aroE-aroC and aroD-aroE on the amounts of the AroD, AroE, and AroC proteins, the strains BW25113 [$P_{tac-10000}$→aroD-aroE-(rpl'D-attB-trpE')-aroC] and BW25113 [$P_{tac-10000}$→aroD-(rpl'D-attB-trpE')-aroE-(rpl'D-attB-trpE')-aroC] was compared to the strain BW25113 [$P_{tac-10000}$→aroD-aroE-aroC]. The DNA fragment from the chromosome of the above-described *E. coli* strain *E. coli* MG1655 [cat-$P_{tac-10000}$→aroD-aroE-aroC] was transferred to the *E. coli* strain BW25113 by P1 transduction to obtain the strain BW25113-[cat-$P_{tac-10000}$→aroD-aroE-aroC] The Cm resistance gene (cat gene) was eliminated from the chromosome BW25113-[cat-$P_{tac-10000}$→aroD-aroE-aroC] strain using the int-xis system as described above (see Example 1, part 5). The obtained strain was named BW25113-[$P_{tac-10000}$→aroD-aroE-aroC].

To estimate the change in the biosynthesis of the AroD, AroE, and AroC proteins in the strains BW25113 [$P_{tac-10000}$→aroD-aroE-aroC], BW25113 [$P_{tac-10000}$→aroD-aroE-(rpl'D-attB-trpE')-aroC] and BW25113 [$P_{tac-10000}$→aroD-(rpl'D-attB-trpE')-aroE-(rpl'D-attB-trpE')-aroC], proteome research was carried out as described in Rabilloud T. Proteome research: Two dimensional gel electrophoresis and identification methods (principals and methods). Springer, N.Y. (2000) as described above (see Example 2).

The results of the proteome research are shown in Table 6. Rates (%) of intensity of spots corresponding to AroD, AroE, and AroC proteins of the total proteins' intensity were normalized for molecular weights of AroD, AroE, and AroC proteins, 27320 Da, 29260 Da, and 38980 Da, respectively. As follows from Table 6, the proportion of the synthesis of AroD, AroE, and AroC proteins is different in the strain BW25113 [$P_{tac-10000}$→aroD-aroE-(rpl'D-attB-trpE')-aroC] и BW25113 [$P_{tac-10000}$→aroD-(rpl'D-attB-trpE')-aroE-(rpl'D-attB-trpE')-aroC] in that it is getting much closer to equimolar in contrast to strain BW25113 [$P_{tac-10000}$→aroD-aroE-aroC]. Translational coupling results in a decrease of the difference between the expression levels of the genes aroD, aroE, and aroC.

While the invention has been described in detail with reference to preferred embodiments thereof, it will be apparent to one skilled in the art that various changes can be made, and equivalents employed, without departing from the scope of the invention. All the cited references herein are incorporated as a part of this application by reference.

TABLE 1

| Cassette | Primers for the first round of PCR | Primers for the second round of PCR | |
|---|---|---|---|
| | | Translational coupling of aroG4-serA5 genes | Translational coupling of zwf-edd genes |
| rplC'D-attR-cat-attL-trpE'D | P5 (SEQ ID NO: 5), P6 (SEQ ID NO: 6) | P7 (SEQ ID NO: 7), P8 (SEQ ID NO: 8) | P23 (SEQ ID NO: 23), P24 (SEQ ID NO: 24) |
| lgt'thyA-attR-cat-attL-trpE'D | P11 (SEQ ID NO: 11), P6 (SEQ ID NO: 6) | P12 (SEQ ID NO: 12), P8 (SEQ ID NO: 8) | P25 (SEQ ID NO: 25), P24 (SEQ ID NO: 24) |
| trpC'B-attR-cat-attL-trpE'D | P13 (SEQ ID NO: 13), P6 (SEQ ID NO: 6) | P14 (SEQ ID NO: 14), P8 (SEQ ID NO: 8) | P26 (SEQ ID NO: 26), P24 (SEQ ID NO: 24) |
| lgt'thyA-attR-cat-attL-trpB'A | P11 (SEQ ID NO: 11), P15 (SEQ ID NO: 15) | P12 (SEQ ID NO: 12), P16 (SEQ ID NO: 16) | P25 (SEQ ID NO: 25), P27 (SEQ ID NO: 27) |
| rplC'D-attR-cat-attL-trpB'A | P5 (SEQ ID NO: 5), P15 (SEQ ID NO: 15) | P7 (SEQ ID NO: 7), P16 (SEQ ID NO: 16) | P23 (SEQ ID NO: 23), P27 (SEQ ID NO: 27) |
| trpC'B-attR-cat-attL-trpB'A | P13 (SEQ ID NO: 13), P15 (SEQ ID NO: 15) | P14 (SEQ ID NO: 14), P16 (SEQ ID NO: 16) | P26 (SEQ ID NO: 26), P27 (SEQ ID NO: 27) |
| rplC'D-attR-cat-attL-thrB'C | P5 (SEQ ID NO: 5), P17 (SEQ ID NO: 17) | P7 (SEQ ID NO: 7), P18 (SEQ ID NO: 18) | P23 (SEQ ID NO: 23), P28 (SEQ ID NO: 28) |
| trpC'B-attR-cat-attL-thrB'C | P13 (SEQ ID NO: 13), P17 (SEQ ID NO: 17) | P14 (SEQ ID NO: 14), P18 (SEQ ID NO: 18) | P26 (SEQ ID NO: 26), P28 (SEQ ID NO: 28) |
| lgt'thyA-attR-cat-attL-thrB'C | P11 (SEQ ID NO: 11), P17 (SEQ ID NO: 17) | P12 (SEQ ID NO: 12), P18 (SEQ ID NO: 18) | P25 (SEQ ID NO: 25), P28 (SEQ ID NO: 28) |
| lgt'thyA-attR-cat-attL-hisH'A | P11 (SEQ ID NO: 11), P19 (SEQ ID NO: 19) | P12 (SEQ ID NO: 12), P20 (SEQ ID NO: 20) | P25 (SEQ ID NO: 25), P29 (SEQ ID NO: 29) |
| rplC'D-attR-cat-attL-hisH'A | P5 (SEQ ID NO: 5), P19 (SEQ ID NO: 19) | P7 (SEQ ID NO: 7), P20 (SEQ ID NO: 20) | P23 (SEQ ID NO: 23), P29 (SEQ ID NO: 29) |
| trpC'B-attR-cat-attL-hisH'A | P13 (SEQ ID NO: 13), P19 (SEQ ID NO: 19) | P14 (SEQ ID NO: 14), P20 (SEQ ID NO: 20) | P26 (SEQ ID NO: 26), P29 (SEQ ID NO: 29) |

TABLE 2

| Strain | Protein | %/MW × 10000 | %/MW × 10000AroG/%/MW × 10000SerA |
|---|---|---|---|
| BW25113 [$P_{tac-ideal}$→aroG4-serA5] | AroG | 0.253 | 10.689 |
| | SerA | 0.024 | |
| BW25113 [$P_{tac-ideal}$→aroG4-(rp1D'-attB-trpE')-serA5] | AroG | 0.297 | 4.170 |
| | SerA | 0.071 | |

TABLE 3

| Solutions | Component | Final concentration, g/l |
|---|---|---|
| A | KH$_2$PO$_4$ | 1.5 |
| | NaCl | 0.5 |
| | (NH$_4$)$_2$SO$_4$ | 1.5 |
| | L-Methionine | 0.05 |
| | L-Phenylalanine | 0.1 |
| | L-Tyrosine | 0.1 |
| | Mameno (total N) | 0.07 |
| B | Glucose | 40.0 |
| | MgSO$_4$ 7H$_2$O | 0.3 |
| C | CaCl$_2$ | 0.011 |
| D | FeSO$_4$ 7H$_2$O | 0.075 |
| | Sodium citrate | 1.0 |
| E | Na$_2$MoO$_4$ 2H$_2$O | 0.00015 |
| | H$_3$BO$_3$ | 0.0025 |
| | CoCl$_2$ 6H$_2$O | 0.00007 |
| | CuSO$_4$ 5H$_2$O | 0.00025 |
| | MnCl$_2$ 4H$_2$O | 0.0016 |
| | ZnSO$_4$ 7H$_2$O | 0.0003 |
| F | Thiamine HCl | 0.005 |
| G | CaCO$_3$ | 30.0 |
| H | Pyridoxine | 0.03 |

The pH of solution A is adjusted to 7.1 with NH$_4$OH.

TABLE 4

| Strain | OD | Trp, g/l |
|---|---|---|
| SV164 | 15.5 ± 1.3 | 1.0 ± 0.2 |
| SV164 [$P_{tac-ideal}$→aroG4-serA5] | 15.9 ± 0.6 | 5.5 ± 0.2 |
| SV164 [$P_{tac-ideal}$→aroG4-(rpl'D-attB-trpE')-serA5] | 16.8 ± 0.5 | 6.2 ± 0.3 |

TABLE 5

| Sequence | Origin |
|---|---|
| 1-450 | Phage Mu attL sequence. |
| 451-502 | The fragment contains the1 bp rest of PstI restriction site, the chromosome region of E. coli including the transcription terminator thrL (452-501 bp) and the 1 bp rest of HindIII restriction site. |
| 503-512 | The HindIII-SphI fragment from the plasmid pUC19. |
| 513-705 | The SphI-BglII fragment from the plasmid pET22b(+) including the part of the tet gene (source - the plasmid pBR322). |
| 706-1081 | The fragment contains the BamHI restriction site, the chromosome region of E. coli including the transcription terminator rrnB (707-1081 bp) and the PstI and BglII restriction sites. |

TABLE 5-continued

| Sequence | Origin |
|---|---|
| 1082-2718 | The sequence of the attR-cat-attL from pMW118-(λattL-Cm$^R$-λattR). |
| 2719-2795 | The BglI-XbaI fragment contains promoter P$_{tac10000}$ where the sequence of "−35" promoter region is TTGACA. |
| 2796-3581 | The fragment EcoRI-NotI contains the chromosome region of E. coli including the aroD gene. |
| 3582-4421 | The fragment NotI-SalI contains the chromosome region of E. coli including the aroE gene. |
| 4422-5544 | The fragment SalI-KpnI contains the chromosome region of E. coli including the aroC gene. |
| 5545-5577 | The fragment KpnI-EcoRI contains the sequence of the attB. |
| 5578-5596 | The rest of artificial polylinker. |
| 5597-6007 | The XbaIpol-AccIpol fragment from the plasmid pML-24[1] contains the two consistent transcription terminators of the bacteriophage fd and the fragment of the plasmid pBR322 (9452-9628 bp). |
| 6008-6140 | The SmaI-PstIpol fragment pMD4041[2] including the part of the bleo gene. |
| 6141-6257 | Phage Mu attR sequence containing the BamHIpol sequence on the 5'-terminus. |

[1] Trukhan et al., Biotechnologiya (in Russian) 4, No. 3 (1988), 325-334.
[2] European patyent application EP20040013414.

TABLE 6

| Strain | Protein | %/MW × 10000 | %/MW × 10000AroD/ %/MW × 10000AroE | %/MW × 10000AroE/ %/MW × 10000AroC |
|---|---|---|---|---|
| BW25113 [P$_{tac-10000}$→aroD-aroE-aroC] | AroD | 0.055 | | |
| | AroE | 0.065 | 0.846 | 3.164 |
| | AroC | 0.021 | | |
| BW25113 [P$_{tac-10000}$→aroD-aroE-(rpl'D-attB-trpE')-aroC] | AroD | 0.040 | | |
| | AroE | 0.048 | 0.842 | 1.243 |
| | AroC | 0.038 | | |
| BW25113 [$_{tac-10000}$→aroD-(rpl'D-attB-trpE')-aroE-(rpl'D-attB-trpE')-aroC] | AroD | 0.037 | | |
| | AroE | 0.041 | 0.893 | 1.332 |
| | AroC | 0.031 | | |

What is claimed:

1. A method for constructing an operon comprising translationally coupled genes comprising:
   A) constructing a DNA fragment comprising an excisable gene coding for a selectable marker flanked by intercistronic regions,
   wherein a first intercistronic region is located upstream of the excisable gene, and said first intercistronic region comprises a first termination codon of a first gene to be translationally coupled, and a first SD-sequence, and a first initiation codon, wherein the first SD-sequence is located upstream of the first initiation codon and downstream of the first termination codon, wherein the first SD sequence can be partially overlapping with the first termination codon,
   and wherein a second intercistronic region is located downstream of the excisable gene, and said second intercistronic region comprises a second termination codon, a second SD-sequence, and a second initiation codon for a second gene to be translationally coupled, wherein the second SD-sequence is located upstream of the second initiation codon and downstream of the second termination codon, wherein the second SD sequence can be partially overlapping with the second initiation codon;
   B) integrating said DNA fragment between said genes to be translationally coupled using homologous recombination; and
   C) excising the gene coding for the selectable marker by a site-specific recombination system, and as a result of said excising, an ORF coding for a peptide results between the genes;
   wherein said intercistronic regions and said genes are from bacteria belonging to the genus *Escherichia*.

2. The method according to claim 1, wherein said first intercistronic region is the intercistronic region between the genes selected from the group consisting of rplC and rplD, trpC and trpB, rplW and rplB, rplB and rpsS, rpsS and rplV, and lgt and thyA; and said second intercistronic region is the intercistronic region between the genes selected from the group consisting of trpE and trpD, trpB and trpA, trpD and trpC, trpC and trpB, thrA and thrB, thrB and thrC, galT and galK, hisG and hisD, hisB and hisH, hisH and hisA, lgt and thyA, rplC and rplD, rplW and rplB, rplB and rpsS, rpsS and rplV, hisD and hisC, hisC and hisB, and rplD and rplW,
   and wherein the second intercistronic region is the intercistronic region between the hisD and hisC genes, hisC and hisB genes, or rplD and rplW genes when the first nucleotide of the second codon of the distal gene is adenosine.

3. The method according to claim 1, wherein said first intercistronic region is the intercistronic region between the rplC and rplD genes and said second intercistronic region is the intercistronic region between the trpE and trpD genes.

4. The method according to claim 1, wherein said homologous recombination in said integrating step comprises the Red-driven integration system.

5. The method according to claim 1, wherein said site-specific recombination system in said excising step comprises the Int/Xis dependent system.

6. The method according to claim 1, wherein said operon is present on a plasmid or in the bacterial chromosome.

7. The method according to claim 1, wherein said operon is bicistronic.

8. The method according to claim 7, wherein said operon comprises the aroG4 and serA5 genes.

9. The method according to claim 1, wherein said operon is tricistronic.

10. The method according to claim 7, wherein said operon comprises the aroD, aroE, and aroC genes.

11. The method according to claim 1, wherein said operon additionally comprises an effective ribosome binding site upstream of the first gene to be translationally coupled.

* * * * *

SEQUENCE LISTING

```
<160> NUMBER OF SEQ ID NOS: 76

<210> SEQ ID NO 1
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gtatggtcta aaggagcag acatgaatta tcagaacgac g                    41

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gacaatcccg ggttacccgc gacgcgcttt tactgc                         36

<210> SEQ ID NO 3
<211> LENGTH: 39
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 3
caacatcccg ggaagacagg attgggtaaa tggcaaagg                             39

<210> SEQ ID NO 4
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ccgttggagc tcgcatgcgt cgacttacag cagacgggcg cgaatgg                   47

<210> SEQ ID NO 5
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aaggagatag caatggcgct gttcgctcaa gttagtataa aaaagctgaa c              51

<210> SEQ ID NO 6
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cagaaagtct cctgttcgat cactgaagcc tgcttttta tactaagttg g               51

<210> SEQ ID NO 7
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gtcaactggc gaatgcagta aaagcgcgtc gcgggtaagg agatagcaat ggcgctgtt      59

<210> SEQ ID NO 8
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cttaatcttg tctttctcca gcgataacctt tgccatcaga aagtctcctg ttcgatcac     59

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 9
tgatggtgga aagccatctg g                                             21

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cgcctttgtg aaattcgatg ttg                                           23

<210> SEQ ID NO 11
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tgaggaacca tggcgctgtt cgctcaagtt agtataaaaa agctgaac                48

<210> SEQ ID NO 12
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gtcaactggc gaatgcagta aaagcgcgtc gcgggtgagg aaccatggcg ctgtt        55

<210> SEQ ID NO 13
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
taaggaaagg aacaatggcg ctgttcgctc aagttagtat aaaaaagctg aac          53

<210> SEQ ID NO 14
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gtcaactggc gaatgcagta aaagcgcgtc gcgggtaagg aaaggaacaa tggcgctgtt   60

<210> SEQ ID NO 15
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
```

```
cagatttccc ctcggatcac tgaagcctgc tttttatac taagttgg                48
```

<210> SEQ ID NO 16
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16

```
cttaatcttg tctttctcca gcgatacctt tgccatcaga tttcccctcg gatcac      56
```

<210> SEQ ID NO 17
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17

```
ttagttttcc aggatcactg aagcctgctt tttatacta agttgg                  46
```

<210> SEQ ID NO 18
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18

```
cttaatcttg tctttctcca gcgatacctt tgccatttag ttttccagga tcactgaagc  60
```

<210> SEQ ID NO 19
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19

```
cacatctcca ggatcactga agcctgcttt tttatactaa gttgg                  45
```

<210> SEQ ID NO 20
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20

```
cttaatcttg tctttctcca gcgatacctt tgccatcaca tctccaggat cactgaag    58
```

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21

```
gacaatgatg cgccgaaacc                                              20
```

```
<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cggtcgaagt tttcgcttgt tc                                              22

<210> SEQ ID NO 23
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ttacccgtga tggtcgttcc tggaatgagt ttgagtaagg agatagcaat ggcgctgtt      59

<210> SEQ ID NO 24
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gattcgattt gttacgcgta acaattgtgg attcatcaga aagtctcctg ttcgatcac     59

<210> SEQ ID NO 25
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ttacccgtga tggtcgttcc tggaatgagt ttgagtgagg aaccatggcg ctgtt          55

<210> SEQ ID NO 26
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ttacccgtga tggtcgttcc tggaatgagt ttgagtaagg aaaggaacaa tggcgctgtt     60

<210> SEQ ID NO 27
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gattcgattt gttacgcgta acaattgtgg attcatcaga tttcccctcg gatcac         56

<210> SEQ ID NO 28
```

```
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gattcgattt gttacgcgta acaattgtgg attcatttag ttttccagga tcactgaagc    60

<210> SEQ ID NO 29
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gattcgattt gttacgcgta acaattgtgg attcatcaca tctccaggat cactgaag      58

<210> SEQ ID NO 30
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gctattccgg gtaccattcg cgcccgtctg ctgtaatgaa gcctgctttt ttatactaag    60
ttgg                                                                 64

<210> SEQ ID NO 31
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gtatcggttt atcagcttgc tttcgaggtg aatttccgct caagttagta taaaaaagct    60
gaac                                                                 64

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tcaccgtcat caccgaaacg                                                20

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
cgcaatatct gcaaacttcc g                                              21
```

<210> SEQ ID NO 34
<211> LENGTH: 2438
<212> TYPE: DNA
<213> ORGANISM: Artificial Sequence
<220> FEATURE:
<223> OTHER INFORMATION: Description of Artificial Sequence: Synthetic ptac-ideal-AroG4-SerA5 sequence polynucleotide

<400> SEQUENCE: 34

```
gtggaattgt gagcgctcac aattccacac ggatctctcc ccatcccct gttgacaatt      60
aatcatcggc tcgtataatg tgtggaattg tgagcggata acaatttcac acaggatcta    120
gaaggagcag acatgaatta tcagaacgac gatttacgca tcaaagaaat caaagagtta    180
cttcctcctg tcgcattgct ggaaaaattc cccgctactg aaaatgccgc gaatacggtt    240
gcccatgccc gaaaagcgat ccataagatc ctgaaaggta atgatgatcg cctgttggtt    300
gtgattggcc catgctcaat tcatgatcct gtcgcggcaa agagtatgc cactcgcttg    360
ctggcgctgc gtgaagagct gaaagatgag ctggaaatcg taatgcgcgt ctattttgaa    420
aagccgcgta ccacggtggg ctggaaaggg ctgattaacg atccgcatat ggataatagc    480
ttccagatca cgacggtct gcgtatagcc cgtaaattgc tgcttgatat taacgacagc    540
ggtctgccag cggcaggtga gtttctcgat atgatcaccc tacaatatct cgctgacctg    600
atgagctggg gcgcaattgg cgcacgtacc accgaatcgc aggtgcaccg cgaactggca    660
tcagggcttt cttgtccggt cggcttcaaa aatggcaccg acggtacgat taaagtggct    720
atcgatgcca ttaatgccgc cggtgcgccg cactgcttcc tgtccgtaac gaaatggggg    780
cattcggcga ttgtgaatac cagcggtaac ggcgattgcc atatcattct gcgcggcggt    840
aaagagccta actacagcgc gaagcacgtt gctgaagtga agaagggct gaacaaagca    900
ggcctgccag cacaggtgat gatcgatttc agccatgcta actcgtccaa acaattcaaa    960
aagcagatgg atgtttgtgc tgacgtttgc cagcagattg ccggtggcga aaaggccatt   1020
attggcgtga tggtggaaag ccatctggtg gaaggcaatc agagcctcga gagcggggag   1080
ccgctggcct acggtaagag catcaccgat gcctgcatcg gctgggaaga taccgatgct   1140
ctgttacgtc aactggcgaa tgcagtaaaa gcgcgtcgcg ggtaacccgg gaagacagga   1200
ttgggtaaat ggcaaaggta tcgctggaga aagacaagat taagttctg ctggtagaag   1260
gcgtgcacca aaaggcgctg aaagccttc gtgcagctgg ttacaccaac atcgaatttc   1320
acaaaggcgc gctggatgat gaacaattaa aagaatccat ccgcgatgcc cacttcatcg   1380
gcctgcgatc ccgtacccat ctgactgaag acgtgatcaa cgccgcagaa aaactggtcg   1440
ctattggctg tttctgtatc ggaacaaacc aggttgatct ggatgcgcg gcaaagcgcg   1500
ggatcccggt atttaacgca ccgttctcaa atacgcgctc tgttgcggag ctggtgattg   1560
gcgaactgct gctgctattg cgcggcgtgc cggaagccaa tgctaaagcg caccgtggcg   1620
tgtggaacaa actggcggcg ggttctttg aagcgcgcgg caaaagctg gtatcatcg   1680
gctacggtca tattggtacg caattgggca ttctggctga atcgctggga atgtatgttt   1740
acttttatga tattgaaaat aaactgccgc tgggcaacgc cactcaggta cagcatcttt   1800
ctgacctgct gaatatgagc gatgtggtga tctgcatgt accagagaat ccgtccacca   1860
aaatatgat gggcgcgaaa gaatttcac taatgaagcc cggctcgctg ctgattaatg   1920
cttcgcgcgg tactgtggtg gatattccgg cgctgtgtga tgcgctggcg agcaaacatc   1980
tggcggggc ggcaatcgac gtattcccga cggaaccggc gaccaatagc gatccattta   2040
cctctccgct gtgtgaattc gacaacgtcc ttctgacgcc acacattggc ggttcgactc   2100
```

```
aggaagcgca ggagaatatc ggcctggaag ttgcgggtaa attgatcaag tattctgaca    2160
atggctcaac gctctctgcg gtgaacttcc cggaagtctc gctgccactg cacggtgggc    2220
gtcgtctgat gcacatccac gaaaaccgtc cgggcgtgct aactgcgctg aacaaaatct    2280
tcgccgagca gggcgtcaac atcgccgcgc aatatctgca aacttccgcc cagatgggtt    2340
atgtggttat tgatattgaa gccgacgaag acgttgccga aaaagcgctg caggcaatga    2400
aagctattcc gggtaccatt cgcgcccgtc tgctgtaa                            2438
```

<210> SEQ ID NO 35
<211> LENGTH: 2490
<212> TYPE: DNA
<213> ORGANISM: Artificial Sequence
<220> FEATURE:
<223> OTHER INFORMATION: Description of Artificial Sequence: Synthetic
      ptac-ideal-AroG4-(rplD-attB-trpE)-SerA5 polynucleotide

<400> SEQUENCE: 35

```
gtggaattgt gagcgctcac aattccacac ggatctctcc ccatccccct gttgacaatt    60
aatcatcggc tcgtataatg tgtggaattg tgagcggata caatttcac acaggatcta    120 gaaggagcag acatgaatta tcagaacgac gatttacgca tcaaagaaat caaagagtta    180
cttcctcctg tcgcattgct ggaaaaattc cccgctactg aaaatgccgc gaatacggtt    240
gcccatgccc gaaaagcgat ccataagatc ctgaaaggta tgatgatcg cctgttggtt    300 gtgattggcc catgctcaat tcatgatcct gtcgcggcaa agagtatgc cactcgcttg    360 ctggcgctgc gtgaagagct gaaagatgag ctggaaatcg taatgcgcgt ctattttgaa    420
aagccgcgta ccacggtggg ctggaaaggg ctgattaacg atccgcatat ggataatagc    480
ttccagatca acgacggtct gcgtatagcc cgtaaattgc tgcttgatat taacgacagc    540
ggtctgccag cggcaggtga gtttctcgat atgatcaccc tacaatatct cgctgacctg    600
atgagctggg gcgcaattgg cgcacgtacc accgaatcgc aggtgcaccg cgaactggca    660
tcagggcttt cttgtccggt cggcttcaaa aatggcaccg acggtacgat taaagtggct    720
atcgatgcca ttaatgccgc cggtgcgccg cactgcttcc tgtccgtaac gaaatggggg    780
cattcggcga ttgtgaatac cagcggtaac ggcgattgcc atatcattct gcgcggcggt    840
aaagagccta actacagcgc gaagcacgtt gctgaagtga agaagggct gaacaaagca    900 ggcctgccag cacaggtgat gatcgatttc agccatgcta actcgtccaa acaattcaaa    960
aagcagatgg atgtttgtgc tgacgtttgc cagcagattg ccggtggcga aaaggccatt    1020
attggcgtga tggtggaaag ccatctggtg gaaggcaatc agagcctcga gcggggag    1080 ccgctggcct acgtaagag catcaccgat gcctgcatcg gctgggaaga taccgatgct    1140
ctgttacgtc aactggcgaa tgcagtaaaa gcgcgtcgcg gtaaggaga tagcaatggc    1200 gctgttcgct caagttagta taaaaaagca ggcttcagtg atcgaacagg agctttctg    1260 atggcaaagg tatcgctgga aaagacaag attaagtttc tgctggtaga aggcgtgcac    1320
caaaaggcgc tggaaagcct tcgtgcagct ggttacacca acatcgaatt tcacaaaggc    1380
gcgctggatg atgaacaatt aaaagaatcc atccgcgatg cccacttcat cggcctgcga    1440
tcccgtaccc atctgactga agacgtgatc aacgccgcag aaaaactggt cgctattggc    1500
tgtttctgta tcggaacaaa ccaggttgat ctggatgcgc ggcaaagcg cgggatcccg    1560 gtatttaacg caccgttctc aaatacgcgc tctgttgcgg agctggtgat tggcgaactg    1620
ctgctgctat tgcgcggcgt gccggaagcc aatgctaaag cgcaccgtgg cgtgtggaac    1680
```

-continued

```
aaactggcgg cggggttcttt tgaagcgcgc ggcaaaaagc tgggtatcat cggctacggt    1740
catattggta cgcaattggg cattctggct gaatcgctgg gaatgtatgt ttactttat     1800 gatattgaaa ataaactgcc gctgggcaac gccactcagg tacagcatct ttctgacctg    1860
ctgaatatga gcgatgtggt gagtctgcat gtaccagaga atccgtccac caaaaatatg    1920
atgggcgcga aagaaatttc actaatgaag cccggctcgc tgctgattaa tgcttcgcgc    1980
ggtactgtgg tggatattcc ggcgctgtgt gatgcgctgg cgagcaaaca tctggcgggg    2040
gcggcaatcg acgtattccc gacggaaccg gcgaccaata gcgatccatt tacctctccg    2100
ctgtgtgaat cgacaacgt ccttctgacg ccacacattg gcggttcgac tcaggaagcg    2160
caggagaata tcggcctgga agttgcgggt aaattgatca agtattctga caatggctca    2220
acgctctctg cggtgaactt cccggaagtc tcgctgccac tgcacggtgg gcgtcgtctg    2280
atgcacatcc acgaaaaccg tccgggcgtg ctaactgcgc tgaacaaaat cttcgccgag    2340
cagggcgtca acatcgccgc gcaatatctg caaacttccg cccagatggg ttatgtggtt    2400
attgatattg aagccgacga agacgttgcc gaaaaagcgc tgcaggcaat gaaagctatt    2460
ccgggtacca ttcgcgcccg tctgctgtaa                                      2490
```

<210> SEQ ID NO 36
<211> LENGTH: 1053
<212> TYPE: DNA
<213> ORGANISM: Escherichia coli
<220> FEATURE:
<221> NAME/KEY: CDS
<222> LOCATION: (1)..(1050)

<400> SEQUENCE: 36

```
atg aat tat cag aac gac gat tta cgc atc aaa gaa atc aaa gag tta        48
Met Asn Tyr Gln Asn Asp Asp Leu Arg Ile Lys Glu Ile Lys Glu Leu
1               5                   10                  15 ctt cct cct gtc gca ttg ctg gaa aaa ttc ccc gct act gaa aat gcc       96
Leu Pro Pro Val Ala Leu Leu Glu Lys Phe Pro Ala Thr Glu Asn Ala
                20                  25                  30 gcg aat acg gtt gcc cat gcc cga aaa gcg atc cat aag atc ctg aaa      144
Ala Asn Thr Val Ala His Ala Arg Lys Ala Ile His Lys Ile Leu Lys
            35                  40                  45 ggt aat gat gat cgc ctg ttg gtt gtg att ggc cca tgc tca att cat      192
Gly Asn Asp Asp Arg Leu Leu Val Val Ile Gly Pro Cys Ser Ile His
        50                  55                  60 gat cct gtc gcg gca aaa gag tat gcc act cgc ttg ctg gcg ctg cgt      240
Asp Pro Val Ala Ala Lys Glu Tyr Ala Thr Arg Leu Leu Ala Leu Arg
65                  70                  75                  80 gaa gag ctg aaa gat gag ctg gaa atc gta atg cgc gtc tat ttt gaa      288
Glu Glu Leu Lys Asp Glu Leu Glu Ile Val Met Arg Val Tyr Phe Glu
                85                  90                  95 aag ccg cgt acc acg gtg ggc tgg aaa ggg ctg att aac gat ccg cat      336
Lys Pro Arg Thr Thr Val Gly Trp Lys Gly Leu Ile Asn Asp Pro His
                100                 105                 110 atg gat aat agc ttc cag atc aac gac ggt ctg cgt ata gcc cgt aaa      384
Met Asp Asn Ser Phe Gln Ile Asn Asp Gly Leu Arg Ile Ala Arg Lys
            115                 120                 125 ttg ctg ctt gat att aac gac agc ggt ctg cca gcg gca ggt gag ttt      432
Leu Leu Leu Asp Ile Asn Asp Ser Gly Leu Pro Ala Ala Gly Glu Phe
        130                 135                 140 ctc gat atg atc acc cca caa tat ctc gct gac ctg atg agc tgg ggc      480
Leu Asp Met Ile Thr Pro Gln Tyr Leu Ala Asp Leu Met Ser Trp Gly
145                 150                 155                 160 gca att ggc gca cgt acc acc gaa tcg cag gtg cac cgc gaa ctg gca      528
```

```
tca ggg ctt tct tgt ccg gtc ggc ttc aaa aat ggc acc gac ggt acg        576
Ser Gly Leu Ser Cys Pro Val Gly Phe Lys Asn Gly Thr Asp Gly Thr
            180                 185                 190 att aaa gtg gct atc gat gcc att aat gcc gcc ggt gcg ccg cac tgc        624
Ile Lys Val Ala Ile Asp Ala Ile Asn Ala Ala Gly Ala Pro His Cys
        195                 200                 205 ttc ctg tcc gta acg aaa tgg ggg cat tcg gcg att gtg aat acc agc        672
Phe Leu Ser Val Thr Lys Trp Gly His Ser Ala Ile Val Asn Thr Ser
    210                 215                 220 ggt aac ggc gat tgc cat atc att ctg cgc ggc ggt aaa gag cct aac        720
Gly Asn Gly Asp Cys His Ile Ile Leu Arg Gly Gly Lys Glu Pro Asn
225                 230                 235                 240 tac agc gcg aag cac gtt gct gaa gtg aaa gaa ggg ctg aac aaa gca        768
Tyr Ser Ala Lys His Val Ala Glu Val Lys Glu Gly Leu Asn Lys Ala
                245                 250                 255 ggc ctg cca gca cag gtg atg atc gat ttc agc cat gct aac tcg tcc        816
Gly Leu Pro Ala Gln Val Met Ile Asp Phe Ser His Ala Asn Ser Ser
            260                 265                 270 aaa caa ttc aaa aag cag atg gat gtt tgt gct gac gtt tgc cag cag        864
Lys Gln Phe Lys Lys Gln Met Asp Val Cys Ala Asp Val Cys Gln Gln
        275                 280                 285 att gcc ggt ggc gaa aag gcc att att ggc gtg atg gtg gaa agc cat        912
Ile Ala Gly Gly Glu Lys Ala Ile Ile Gly Val Met Val Glu Ser His
    290                 295                 300 ctg gtg gaa ggc aat cag agc ctc gag agc ggg gag ccg ctg gcc tac        960
Leu Val Glu Gly Asn Gln Ser Leu Glu Ser Gly Glu Pro Leu Ala Tyr
305                 310                 315                 320 ggt aag agc atc acc gat gcc tgc atc ggc tgg gaa gat acc gat gct       1008
Gly Lys Ser Ile Thr Asp Ala Cys Ile Gly Trp Glu Asp Thr Asp Ala
                325                 330                 335 ctg tta cgt caa ctg gcg aat gca gta aaa gcg cgt cgc ggg taa           1053
Leu Leu Arg Gln Leu Ala Asn Ala Val Lys Ala Arg Arg Gly
            340                 345                 350

<210> SEQ ID NO 37
<211> LENGTH: 350
<212> TYPE: PRT
<213> ORGANISM: Escherichia coli

<400> SEQUENCE: 37

Met Asn Tyr Gln Asn Asp Asp Leu Arg Ile Lys Glu Ile Lys Glu Leu
1               5                   10                  15

Leu Pro Pro Val Ala Leu Leu Glu Lys Phe Pro Ala Thr Glu Asn Ala
            20                  25                  30

Ala Asn Thr Val Ala His Ala Arg Lys Ala Ile His Lys Ile Leu Lys
        35                  40                  45

Gly Asn Asp Asp Arg Leu Leu Val Val Ile Gly Pro Cys Ser Ile His
    50                  55                  60

Asp Pro Val Ala Ala Lys Glu Tyr Ala Thr Arg Leu Leu Ala Leu Arg
65                  70                  75                  80

Glu Glu Leu Lys Asp Glu Leu Glu Ile Val Met Arg Val Tyr Phe Glu
                85                  90                  95

Lys Pro Arg Thr Thr Val Gly Trp Lys Gly Leu Ile Asn Asp Pro His
            100                 105                 110

Met Asp Asn Ser Phe Gln Ile Asn Asp Gly Leu Arg Ile Ala Arg Lys
        115                 120                 125

Leu Leu Leu Asp Ile Asn Asp Ser Gly Leu Pro Ala Ala Gly Glu Phe
```

```
                130                 135                 140
Leu Asp Met Ile Thr Pro Gln Tyr Leu Ala Asp Leu Met Ser Trp Gly
145                 150                 155                 160

Ala Ile Gly Ala Arg Thr Thr Glu Ser Gln Val His Arg Glu Leu Ala
                165                 170                 175

Ser Gly Leu Ser Cys Pro Val Gly Phe Lys Asn Gly Thr Asp Gly Thr
            180                 185                 190

Ile Lys Val Ala Ile Asp Ala Ile Asn Ala Ala Gly Ala Pro His Cys
        195                 200                 205

Phe Leu Ser Val Thr Lys Trp Gly His Ser Ala Ile Val Asn Thr Ser
    210                 215                 220

Gly Asn Gly Asp Cys His Ile Ile Leu Arg Gly Gly Lys Glu Pro Asn
225                 230                 235                 240

Tyr Ser Ala Lys His Val Ala Glu Val Lys Glu Gly Leu Asn Lys Ala
                245                 250                 255

Gly Leu Pro Ala Gln Val Met Ile Asp Phe Ser His Ala Asn Ser Ser
            260                 265                 270

Lys Gln Phe Lys Lys Gln Met Asp Val Cys Ala Asp Val Cys Gln Gln
        275                 280                 285

Ile Ala Gly Gly Glu Lys Ala Ile Ile Gly Val Met Val Glu Ser His
    290                 295                 300

Leu Val Glu Gly Asn Gln Ser Leu Glu Ser Gly Glu Pro Leu Ala Tyr
305                 310                 315                 320

Gly Lys Ser Ile Thr Asp Ala Cys Ile Gly Trp Glu Asp Thr Asp Ala
                325                 330                 335

Leu Leu Arg Gln Leu Ala Asn Ala Val Lys Ala Arg Gly
            340                 345                 350

<210> SEQ ID NO 38
<211> LENGTH: 1233
<212> TYPE: DNA
<213> ORGANISM: Escherichia coli
<220> FEATURE:
<221> NAME/KEY: CDS
<222> LOCATION: (1)..(1230)

<400> SEQUENCE: 38 atg gca aag gta tcg ctg gag aaa gac aag att aag ttt ctg ctg gta        48
Met Ala Lys Val Ser Leu Glu Lys Asp Lys Ile Lys Phe Leu Leu Val
1               5                   10                  15 gaa ggc gtg cac caa aag gcg ctg gaa agc ctt cgt gca gct ggt tac        96
Glu Gly Val His Gln Lys Ala Leu Glu Ser Leu Arg Ala Ala Gly Tyr
                20                  25                  30 acc aac atc gaa ttt cac aaa ggc gcg ctg gat gat gaa caa tta aaa       144
Thr Asn Ile Glu Phe His Lys Gly Ala Leu Asp Asp Glu Gln Leu Lys
            35                  40                  45 gaa tcc atc cgc gat gcc cac ttc atc ggc ctg cga tcc cgt acc cat       192
Glu Ser Ile Arg Asp Ala His Phe Ile Gly Leu Arg Ser Arg Thr His
        50                  55                  60 ctg act gaa gac gtg atc aac gcc gca gaa aaa ctg gtc gct att ggc       240
Leu Thr Glu Asp Val Ile Asn Ala Ala Glu Lys Leu Val Ala Ile Gly
65                  70                  75                  80 tgt ttc tgt atc gga aca aac cag gtt gat ctg gat gcg gcg gca aag       288
Cys Phe Cys Ile Gly Thr Asn Gln Val Asp Leu Asp Ala Ala Ala Lys
                85                  90                  95 cgc ggg atc ccg gta ttt aac gca ccg ttc tca aat acg cgc tct gtt       336
Arg Gly Ile Pro Val Phe Asn Ala Pro Phe Ser Asn Thr Arg Ser Val
            100                 105                 110
```

| | | |
|---|---|---|
| gcg gag ctg gtg att ggc gaa ctg ctg ctg cta ttg cgc ggc gtg ccg<br>Ala Glu Leu Val Ile Gly Glu Leu Leu Leu Leu Arg Gly Val Pro<br>115                      120                      125 | | 384 |
| gaa gcc aat gct aaa gcg cac cgt ggc gtg tgg aac aaa ctg gcg gcg<br>Glu Ala Asn Ala Lys Ala His Arg Gly Val Trp Asn Lys Leu Ala Ala<br>130                      135                      140 | | 432 |
| ggt tct ttt gaa gcg cgc ggc aaa aag ctg ggt atc atc ggc tac ggt<br>Gly Ser Phe Glu Ala Arg Gly Lys Lys Leu Gly Ile Ile Gly Tyr Gly<br>145                      150                      155                      160 | | 480 |
| cat att ggt acg caa ttg ggc att ctg gct gaa tcg ctg gga atg tat<br>His Ile Gly Thr Gln Leu Gly Ile Leu Ala Glu Ser Leu Gly Met Tyr<br>                      165                      170                      175 | | 528 |
| gtt tac ttt tat gat att gaa aat aaa ctg ccg ctg ggc aac gcc act<br>Val Tyr Phe Tyr Asp Ile Glu Asn Lys Leu Pro Leu Gly Asn Ala Thr<br>                      180                      185                      190 | | 576 |
| cag gta cag cat ctt tct gac ctg ctg aat atg agc gat gtg gtg agt<br>Gln Val Gln His Leu Ser Asp Leu Leu Asn Met Ser Asp Val Val Ser<br>                      195                      200                      205 | | 624 |
| ctg cat gta cca gag aat ccg tcc acc aaa aat atg atg ggc gcg aaa<br>Leu His Val Pro Glu Asn Pro Ser Thr Lys Asn Met Met Gly Ala Lys<br>210                      215                      220 | | 672 |
| gaa att tca cta atg aag ccc ggc tcg ctg ctg att aat gct tcg cgc<br>Glu Ile Ser Leu Met Lys Pro Gly Ser Leu Leu Ile Asn Ala Ser Arg<br>225                      230                      235                      240 | | 720 |
| ggt act gtg gtg gat att ccg gcg ctg tgt gat gcg ctg gcg agc aaa<br>Gly Thr Val Val Asp Ile Pro Ala Leu Cys Asp Ala Leu Ala Ser Lys<br>                      245                      250                      255 | | 768 |
| cat ctg gcg ggg gcg gca atc gac gta ttc ccg acg gaa ccg gcg acc<br>His Leu Ala Gly Ala Ala Ile Asp Val Phe Pro Thr Glu Pro Ala Thr<br>                      260                      265                      270 | | 816 |
| aat agc gat cca ttt acc tct ccg ctg tgt gaa ttc gac aac gtc ctt<br>Asn Ser Asp Pro Phe Thr Ser Pro Leu Cys Glu Phe Asp Asn Val Leu<br>                      275                      280                      285 | | 864 |
| ctg acg cca cac att ggc ggt tcg act cag gaa gcg cag gag aat atc<br>Leu Thr Pro His Ile Gly Gly Ser Thr Gln Glu Ala Gln Glu Asn Ile<br>                      290                      295                      300 | | 912 |
| ggc ctg gaa gtt gcg ggt aaa ttg atc aag tat tct gac aat ggc tca<br>Gly Leu Glu Val Ala Gly Lys Leu Ile Lys Tyr Ser Asp Asn Gly Ser<br>305                      310                      315                      320 | | 960 |
| acg ctc tct gcg gtg aac ttc ccg gaa gtc tcg ctg cca ctg cac ggt<br>Thr Leu Ser Ala Val Asn Phe Pro Glu Val Ser Leu Pro Leu His Gly<br>                      325                      330                      335 | | 1008 |
| ggg cgt cgt ctg atg cac atc cac gaa aac cgt ccg ggc gtg cta act<br>Gly Arg Arg Leu Met His Ile His Glu Asn Arg Pro Gly Val Leu Thr<br>                      340                      345                      350 | | 1056 |
| gcg ctg aac aaa atc ttc gcc gag cag ggc gtc aac atc gcc gcg caa<br>Ala Leu Asn Lys Ile Phe Ala Glu Gln Gly Val Asn Ile Ala Ala Gln<br>                      355                      360                      365 | | 1104 |
| tat ctg caa act tcc gcc cag atg ggt tat gtg gtt att gat att gaa<br>Tyr Leu Gln Thr Ser Ala Gln Met Gly Tyr Val Val Ile Asp Ile Glu<br>370                      375                      380 | | 1152 |
| gcc gac gaa gac gtt gcc gaa aaa gcg ctg cag gca atg aaa gct att<br>Ala Asp Glu Asp Val Ala Glu Lys Ala Leu Gln Ala Met Lys Ala Ile<br>385                      390                      395                      400 | | 1200 |
| ccg ggt acc att cgc gcc cgt ctg ctg tac taa<br>Pro Gly Thr Ile Arg Ala Arg Leu Leu Tyr<br>                      405                      410 | | 1233 |

<210> SEQ ID NO 39
<211> LENGTH: 410
<212> TYPE: PRT

<213> ORGANISM: Escherichia coli

<400> SEQUENCE: 39

Met Ala Lys Val Ser Leu Glu Lys Asp Lys Ile Lys Phe Leu Leu Val
1               5                   10                  15

Glu Gly Val His Gln Lys Ala Leu Glu Ser Leu Arg Ala Ala Gly Tyr
            20                  25                  30

Thr Asn Ile Glu Phe His Lys Gly Ala Leu Asp Asp Glu Gln Leu Lys
        35                  40                  45

Glu Ser Ile Arg Asp Ala His Phe Ile Gly Leu Arg Ser Arg Thr His
    50                  55                  60

Leu Thr Glu Asp Val Ile Asn Ala Ala Glu Lys Leu Val Ala Ile Gly
65                  70                  75                  80

Cys Phe Cys Ile Gly Thr Asn Gln Val Asp Leu Asp Ala Ala Ala Lys
                85                  90                  95

Arg Gly Ile Pro Val Phe Asn Ala Pro Phe Ser Asn Thr Arg Ser Val
            100                 105                 110

Ala Glu Leu Val Ile Gly Glu Leu Leu Leu Leu Arg Gly Val Pro
        115                 120                 125

Glu Ala Asn Ala Lys Ala His Arg Gly Val Trp Asn Lys Leu Ala Ala
    130                 135                 140

Gly Ser Phe Glu Ala Arg Gly Lys Lys Leu Gly Ile Ile Gly Tyr Gly
145                 150                 155                 160

His Ile Gly Thr Gln Leu Gly Ile Leu Ala Glu Ser Leu Gly Met Tyr
                165                 170                 175

Val Tyr Phe Tyr Asp Ile Glu Asn Lys Leu Pro Leu Gly Asn Ala Thr
            180                 185                 190

Gln Val Gln His Leu Ser Asp Leu Leu Asn Met Ser Asp Val Val Ser
        195                 200                 205

Leu His Val Pro Glu Asn Pro Ser Thr Lys Asn Met Met Gly Ala Lys
    210                 215                 220

Glu Ile Ser Leu Met Lys Pro Gly Ser Leu Leu Ile Asn Ala Ser Arg
225                 230                 235                 240

Gly Thr Val Val Asp Ile Pro Ala Leu Cys Asp Ala Leu Ala Ser Lys
                245                 250                 255

His Leu Ala Gly Ala Ala Ile Asp Val Phe Pro Thr Glu Pro Ala Thr
            260                 265                 270

Asn Ser Asp Pro Phe Thr Ser Pro Leu Cys Glu Phe Asp Asn Val Leu
        275                 280                 285

Leu Thr Pro His Ile Gly Gly Ser Thr Gln Glu Ala Gln Glu Asn Ile
    290                 295                 300

Gly Leu Glu Val Ala Gly Lys Leu Ile Lys Tyr Ser Asp Asn Gly Ser
305                 310                 315                 320

Thr Leu Ser Ala Val Asn Phe Pro Glu Val Ser Leu Pro Leu His Gly
                325                 330                 335

Gly Arg Arg Leu Met His Ile His Glu Asn Arg Pro Gly Val Leu Thr
            340                 345                 350

Ala Leu Asn Lys Ile Phe Ala Glu Gln Gly Val Asn Ile Ala Ala Gln
        355                 360                 365

Tyr Leu Gln Thr Ser Ala Gln Met Gly Tyr Val Val Ile Asp Ile Glu
    370                 375                 380

Ala Asp Glu Asp Val Ala Glu Lys Ala Leu Gln Ala Met Lys Ala Ile
385                 390                 395                 400

Pro Gly Thr Ile Arg Ala Arg Leu Leu Tyr

```
<210> SEQ ID NO 40
<211> LENGTH: 17
<212> TYPE: DNA
<213> ORGANISM: Unknown
<220> FEATURE:
<223> OTHER INFORMATION: Description of Unknown: trpE-D junction
      sequence

<400> SEQUENCE: 40
caggagactt tctgatg                                                  17

<210> SEQ ID NO 41
<211> LENGTH: 17
<212> TYPE: DNA
<213> ORGANISM: Unknown
<220> FEATURE:
<223> OTHER INFORMATION: Description of Unknown: trpB-A junction
      sequence

<400> SEQUENCE: 41 cgagggaaa tctgatg                                                   17

<210> SEQ ID NO 42
<211> LENGTH: 15
<212> TYPE: DNA
<213> ORGANISM: Unknown
<220> FEATURE:
<223> OTHER INFORMATION: Description of Unknown: trpD-C junction
      sequence

<400> SEQUENCE: 42
gcacgagggt aaatg                                                    15

<210> SEQ ID NO 43
<211> LENGTH: 17
<212> TYPE: DNA
<213> ORGANISM: Unknown
<220> FEATURE:
<223> OTHER INFORMATION: Description of Unknown: trpC-B junction
      sequence

<400> SEQUENCE: 43
taaggaaagg aacaatg                                                  17

<210> SEQ ID NO 44
<211> LENGTH: 16
<212> TYPE: DNA
<213> ORGANISM: Unknown
<220> FEATURE:
<223> OTHER INFORMATION: Description of Unknown: thrA-B junction
      sequence

<400> SEQUENCE: 44
ttaggagtct gacatg                                                   16

<210> SEQ ID NO 45
<211> LENGTH: 15
<212> TYPE: DNA
<213> ORGANISM: Unknown
<220> FEATURE:
<223> OTHER INFORMATION: Description of Unknown: thrB-C junction
      sequence

<400> SEQUENCE: 45
ctggaaaact aaatg                                                    15
```

```
<210> SEQ ID NO 46
<211> LENGTH: 16
<212> TYPE: DNA
<213> ORGANISM: Unknown
<220> FEATURE:
<223> OTHER INFORMATION: Description of Unknown: galT-K junction
      sequence

<400> SEQUENCE: 46
ggagtgtaag aaatga                                                     16

<210> SEQ ID NO 47
<211> LENGTH: 17
<212> TYPE: DNA
<213> ORGANISM: Unknown
<220> FEATURE:
<223> OTHER INFORMATION: Description of Unknown: hisG-D junction
      sequence

<400> SEQUENCE: 47
atggagtgat cgccatg                                                    17

<210> SEQ ID NO 48
<211> LENGTH: 18
<212> TYPE: DNA
<213> ORGANISM: Unknown
<220> FEATURE:
<223> OTHER INFORMATION: Description of Unknown: hisD-C junction
      sequence

<400> SEQUENCE: 48
cttaaggagc aagcatga                                                   18

<210> SEQ ID NO 49
<211> LENGTH: 15
<212> TYPE: DNA
<213> ORGANISM: Unknown
<220> FEATURE:
<223> OTHER INFORMATION: Description of Unknown: hisC-B junction
      sequence

<400> SEQUENCE: 49
gcggagcaag tttga                                                      15

<210> SEQ ID NO 50
<211> LENGTH: 17
<212> TYPE: DNA
<213> ORGANISM: Unknown
<220> FEATURE:
<223> OTHER INFORMATION: Description of Unknown: hisB-H junction
      sequence

<400> SEQUENCE: 50
aaaggagtgc tgtaatg                                                    17

<210> SEQ ID NO 51
<211> LENGTH: 14
<212> TYPE: DNA
<213> ORGANISM: Unknown
<220> FEATURE:
<223> OTHER INFORMATION: Description of Unknown: hisH-A junction
      sequence

<400> SEQUENCE: 51
ctggagatgt gatg                                                       14

<210> SEQ ID NO 52
```

```
<211> LENGTH: 12
<212> TYPE: DNA
<213> ORGANISM: Unknown
<220> FEATURE:
<223> OTHER INFORMATION: Description of Unknown: lgt-thyA junction
      sequence

<400> SEQUENCE: 52
tgaggaacca tg                                                          12

<210> SEQ ID NO 53
<211> LENGTH: 16
<212> TYPE: DNA
<213> ORGANISM: Unknown
<220> FEATURE:
<223> OTHER INFORMATION: Description of Unknown: rplC-D junction
      sequence

<400> SEQUENCE: 53
taaggagata gcaatg                                                      16

<210> SEQ ID NO 54
<211> LENGTH: 18
<212> TYPE: DNA
<213> ORGANISM: Unknown
<220> FEATURE:
<223> OTHER INFORMATION: Description of Unknown: rplD-W junction
      sequence

<400> SEQUENCE: 54
gaggagatgc tggcatga                                                    18

<210> SEQ ID NO 55
<211> LENGTH: 23
<212> TYPE: DNA
<213> ORGANISM: Unknown
<220> FEATURE:
<223> OTHER INFORMATION: Description of Unknown: rplW-B junction
      sequence

<400> SEQUENCE: 55
taagtcggag gagtaataca atg                                              23

<210> SEQ ID NO 56
<211> LENGTH: 22
<212> TYPE: DNA
<213> ORGANISM: Unknown
<220> FEATURE:
<223> OTHER INFORMATION: Description of Unknown: rplB-rpsS junction
      sequence

<400> SEQUENCE: 56
taattttaga ggataagcca tg                                               22

<210> SEQ ID NO 57
<211> LENGTH: 20
<212> TYPE: DNA
<213> ORGANISM: Unknown
<220> FEATURE:
<223> OTHER INFORMATION: Description of Unknown: rpsS-rplV junction
      sequence

<400> SEQUENCE: 57
taaggtagga ggaagagatg                                                  20

<210> SEQ ID NO 58
<211> LENGTH: 81
<212> TYPE: DNA
```

```
<213> ORGANISM: Artificial Sequence
<220> FEATURE:
<223> OTHER INFORMATION: Description of Artificial Sequence: Synthetic
      rplCD junction, attB site and trpED junction
      oligonucleotide
<220> FEATURE:
<221> NAME/KEY: CDS
<222> LOCATION: (14)..(76)

<400> SEQUENCE: 58
taaggagata gca atg gcg ctg ttc gct caa gtt agt ata aaa aag cag        49
            Met Ala Leu Phe Ala Gln Val Ser Ile Lys Lys Gln
              1               5                  10 gct tca gtg atc gaa cag gag act ttc tgatg                            81
Ala Ser Val Ile Glu Gln Glu Thr Phe
         15                  20

<210> SEQ ID NO 59
<211> LENGTH: 21
<212> TYPE: PRT
<213> ORGANISM: Artificial Sequence
<220> FEATURE:
<223> OTHER INFORMATION: Description of Artificial Sequence: Synthetic
      rplCD junction, attB site and trpED junction peptide

<400> SEQUENCE: 59

Met Ala Leu Phe Ala Gln Val Ser Ile Lys Lys Gln Ala Ser Val Ile
  1               5                  10                  15

Glu Gln Glu Thr Phe
             20

<210> SEQ ID NO 60
<211> LENGTH: 6257
<212> TYPE: DNA
<213> ORGANISM: Artificial Sequence
<220> FEATURE:
<223> OTHER INFORMATION: Description of Artificial Sequence: Synthetic
      operon cat-Ptac-10000-aroD-aroE-aroC polynucleotide

<400> SEQUENCE: 60
tgtattgatt cacttgaagt acgaaaaaaa ccgggaggac attggattat tcgggatctg      60
atgggattag atttggtggg gcttgcaagc ctgtagtgca aattttagtc gttaatcaat     120
gaaacgcgaa agatagtaaa aaattgcttt tgtttcattg aaaatacgaa aaacaaaaac     180
actgcaaatc atttcaataa cagcttcaaa aaacgttcaa aaccgataac aaccaagctg     240
tcaccaaatg actcatatca caaatcagct tatgccgttt aggtatgtta catgtgtgat     300
tatgtgaggt gaagtatgtt ttagctggtt catggttgtt atacggcttt ttttacctcc     360
tgtggttcct gtgaaggtac tacaacactt tcctgttcat gaatcccata ctttgacaaa     420
atctctttgc gttttcttc aggtaatgca gtggtcgaaa aaaaaagccc gcactgtcag      480
gtgcgggctt ttttctgtgt taagcttgca tgcaaggaga tggcgcccaa cagtcccccg     540
gccacggggc ctgccaccat acccacgccg aaacaagcgc tcatgagccc gaagtggcga     600
gcccgatctt ccccatcggt gatgtcggcg atataggcgc cagcaaccgc acctgtggcg     660
ccggtgatgc cggccacgat gcgtccgcg tagaggatcg agatcctttg cctggcggca      720
gtagcgcggc agtttgcctg gcggcagtag cgcggtggtc ccacctgacc ccatgccgaa     780
ctcagaagtg aaacgccgta gcgccgatgg tagtgtgggg tctccccatg cgagagtagg     840
gaactgccag gcatcaaata aaacgaaagg ctcagtcgaa agactgggcc tttcgtttta     900
tctgttgttt tcggtgaacg ctctcctgag taggacaaat ccgccgggag cggatttgaa     960
cgttgcgaag caacggcccg gagggtggcg gcaggacgc ccgccataaa ctgccaggca     1020
```

| | | | | |
|---|---|---|---|---|
| tcaaattaag | cagaaggcca | tcctgacgga | tggcctttt | gcgtttctac aaactctttt | 1080 |
| tcgctcaagt | tagtataaaa | aagctgaacg | agaaacgtaa | aatgatataa atatcaatat | 1140 |
| attaaattag | attttgcata | aaaaacagac | tacataatac | tgtaaaacac aacatatgca | 1200 |
| gtcactatga | atcaactact | tagatggtat | tagtgacctg | taacagactg cagtggtcga | 1260 |
| aaaaaaaagc | ccgcactgtc | aggtgcgggc | ttttttctgt | gttaagcttc gacgaatttc | 1320 |
| tgccattcat | ccgcttatta | tcacttattc | aggcgtagca | ccaggcgttt aagggcacca | 1380 |
| ataactgcct | taaaaaaatt | acgcccgcc | ctgccactca | tcgcagtact gttgtaattc | 1440 |
| attaagcatt | ctgccgacat | ggaagccatc | acagacggca | tgatgaacct gaatcgccag | 1500 |
| cggcatcagc | accttgtcgc | cttgcgtata | atattgccc | atggtgaaaa cggggcgaa | 1560 |
| gaagttgtcc | atattggcca | cgtttaaatc | aaaactggtg | aaactcaccc agggattggc | 1620 |
| tgagacgaaa | aacatattct | caataaaccc | tttagggaaa | taggccaggt tttcaccgta | 1680 |
| acacgccaca | tcttgcgaat | atatgtgtag | aaactgccgg | aaatcgtcgt ggtattcact | 1740 |
| ccagagcgat | gaaaacgttt | cagtttgctc | atggaaaacg | gtgtaacaag ggtgaacact | 1800 |
| atcccatatc | accagctcac | cgtctttcat | tgccatacgg | aattccggat gagcattcat | 1860 |
| caggcgggca | agaatgtgaa | taaaggccgg | ataaaacttg | tgcttatttt tctttacggt | 1920 |
| ctttaaaaag | gccgtaatat | ccagctgaac | ggtctggtta | taggtacatt gagcaactga | 1980 |
| ctgaaatgcc | tcaaaatgtt | ctttacgatg | ccattgggat | atatcaacgg tggtatatcc | 2040 |
| agtgatttt | ttctccattt | tagcttcctt | agctcctgaa | atctcggat ccggccaagc | 2100 |
| tagcttggct | ctagagcgcc | cggttgacgc | tgctagtgtt | acctagcgat ttgtatctta | 2160 |
| ctgcatgtta | cttcatgttg | tcaataccctg | ttttcgtgc | gacttatcag gctgtctact | 2220 |
| tatccggaga | tccacaggac | gggtgtggtc | gccatgatcg | cgtagtcgat agtggctcca | 2280 |
| agtagcgaag | cgagcaggac | tgggcggcgg | ccaaagcggt | cggacagtgc tccgagaacg | 2340 |
| ggtgcgcata | gaaattgcat | caacgcatat | agcgctagca | gcacgccata gtgactggcg | 2400 |
| atgctgtcgg | aatggacgat | atcccgcaag | aggcccggca | gtaccggcat aaccaagcct | 2460 |
| atgcctacag | catccagggt | gacggtgccg | aggatgacga | tgagcgcatt gttagatttc | 2520 |
| atacacggtg | cctgactgcg | ttagcaattt | aactgtgata | aactaccgca ttaaagctta | 2580 |
| tcgatgataa | gctgtcaaac | atgagaattc | gaaatcaaat | aatgatttta ttttgactga | 2640 |
| tagtgacctg | ttcgttgcaa | caaattgata | agcaatgctt | ttttataatg ccaacttagt | 2700 |
| ataaaaagc | aggcttcaag | atctccctgt | tgacaattaa | tcatcggctc gtataatgtg | 2760 |
| tggaattgtg | agcggataac | aatttcacac | aggatctaga | gcgtgcagaa agggtaaaaa | 2820 |
| atgaaaaccg | taactgtaaa | agatctcgtc | attggtacgg | gcgcacctaa aatcatcgtc | 2880 |
| tcgctgatgg | cgaaagatat | cgccagcgtg | aaatccgaag | ctctcgccta tcgtgaagcg | 2940 |
| gactttgata | ttctggaatg | gcgtgtggac | cactatgccg | acctctccaa tgtggagtct | 3000 |
| gtcatggcgg | cagcaaaaat | tctccgtgag | accatgccag | aaaaaccgct gctgtttacc | 3060 |
| ttccgcagtg | ccaaagaagg | cggcgagcag | gcgatttcca | ccgaggctta tattgcactc | 3120 |
| aatcgtgcag | ccatcgacag | cggcctggtt | gatatgatcg | atctggagtt atttaccggt | 3180 |
| gatgatcagg | ttaaagaaac | cgtcgcctac | gcccacgcgc | atgatgtgaa agtagtcatg | 3240 |
| tccaaccatg | acttccataa | aacgccggaa | gccgaagaaa | tcattgcccg tctgcgcaaa | 3300 |
| atgcaatcct | tcgacgccga | tattcctaag | attgcgctga | tgccgcaaag taccagcgat | 3360 |
| gtgctgacgt | tgcttgccgc | gaccctggag | atgcaggagc | agtatgccga tcgtccaatt | 3420 |

```
atcacgatgt cgatggcaaa aactggcgta atttctcgtc tggctggtga agtatttggc   3480
tcggcggcaa cttttggtgc ggtaaaaaaa gcgtctgcgc cagggcaaat ctcggtaaat   3540
gatttgcgca cggtattaac tattttacac caggcataag cggccgcaca ggagtaacat   3600
aatggaaacc tatgctgttt ttggtaatcc gatagcccac agcaaatcgc cattcattca   3660
tcagcaattt gctcagcaac tgaatattga acatccctat gggcgcgtgt tggcacccat   3720
caatgatttc atcaacacac tgaacgcttt ctttagtgct ggtggtaaag gtgcgaatgt   3780
gacggtgcct tttaaagaag aggcttttgc cagagcggat gagcttactg aacgggcagc   3840
gttggctggt gctgttaata ccctcatgcg gttagaagat ggacgcctgc tgggtgacaa   3900
taccgatggt gtaggcttgt taagcgatct ggaacgtctg tcttttatcc gccctggttt   3960
acgtattctg cttatcggcg ctggtggagc atctcgcggc gtactactgc cactcctttc   4020
cctggactgt gcggtgacaa taactaatcg gacggtatcc cgcgcggaag agttggctaa   4080
attgtttgcg cacactggca gtattcaggc gttgagtatg gacgaactgg aaggtcatga   4140
gtttgatctc attattaatg caacatccag tggcatcagt ggtgatattc cggcgatccc   4200
gtcatcgctc attcatccag gcatttattg ctatgacatg ttctatcaga aaggaaaaac   4260 tcctttctg gcatggtgtg agcagcgagg ctcaaagcgt aatgctgatg gtttaggaat   4320
gctggtggca caggcggctc atgcctttct tctctggcac ggtgttctgc ctgacgtaga   4380
accagttata aagcaattgc aggaggaatt gtccgcgtga gtcgactcta gctagaggat   4440
ctaaggagcc gtgatggctg gaaacacaat tggacaactc tttcgcgtaa ccaccttcgg   4500
cgaatcgcac gggctggcgc tcggctgcat cgtcgatggt gttccgccag gcattccgct   4560
gacggaagcg gacctgcaac atgacctcga ccgtcgtcgc cctgggacat cgcgctatac   4620
cacccagcgc cgcgagccgg atcaggtcaa aattctctcc ggtgttttg aaggcgttac   4680 taccggcacc agcattggct tgttgatcga aaacactgac cagcgctctc aggattacag   4740
tgcgattaag gacgttttcc gtccaggcca tgccgattac acctacgaac aaaaatacgg   4800
tctgcgcgat tatcgcggcg gtggacgttc ttccgcccgc gaaaccgcca tgcgcgtggc   4860
ggcaggagct attgccaaaa atatctcgc cgagaaattt ggtattgaaa tccgtggctg   4920
cctgacccag atgggcgaca ttccgctgga tatcaaagac tggtcgcagg tcgagcaaaa   4980 tccgttttt tgcccggacc ccgacaaaat cgacgcgtta gacgagttga tgcgtgcgct   5040 gaaaaagag ggcgactcca tcggcgctaa agtcaccgtt gttgccagtg gcgttcctgc   5100
cggacttggc gagccggtct ttgaccgcct ggatgctgac atcgcccatg cgctgatgag   5160
catcaacgcg gtgaaaggcg tggaaattgg cgacggcttt gacgtggtgg cgctgcgcgg   5220
cagccagaac cgcgatgaaa tcaccaaaga cggtttccag agcaaccatg cgggcggcat   5280
tctcggcggt atcagcagcg ggcagcaaat cattgcccat atggcgctga accgacctc   5340 cagcattacc gtgccgggtc gtaccattaa ccgctttggc gaagaagttg agatgatcac   5400
caaaggccgt cacgatccct gtgtcggat ccgcgcagtg ccgatcgcag aagcgatgct   5460
ggcgatcgtt ttaatggatc acctgttacg gcaacgggcg caaaatgccg atgtgaagac   5520
tgatattcca cgctggtaag gtacctgaag cctgctttt tatactaact tgagcggaat   5580
tcaacggtaa ttctagctag agtcgaaatt cacctcgaaa gcaagctgat aaaccgatac   5640
aattaaaggc tccttttgga gccttttttt ttggagattt tcaacgtgaa aaaattatta   5700
ttcgcaattc aagctaattc acctcgaaag caagctgata aaccgataca attaaaggct   5760 cctttggag ccttttttt tggagatttt caacgtgaaa aaattattat tcgcaattcc   5820
```

```
aagctctgcc tcgcgcgttt cggtgatgac ggtgaaaacc tctgacacat gcagctcccg    5880
gagacggtca cagcttgtct gtaagcggat gccgggagca gacaagcccg tcagggcgcg    5940
tcagcgggtg ttggcgggtg tcggggcgca gccatgaccc agtcacgtag cgatagcgga    6000
gtgtataggg ctcgatcccc tcgcgagttg gttcagctgc tgcctgaggc tggacgacct    6060
cgcggagttc taccggcagt gcaaatccgt cggcatccag gaaaccagca gcggctatcc    6120
gcgcatccat gccccgaac gatccccatg taatgaataa aaagcagtaa ttaatacatc    6180
tgtttcattt gaagcgcgaa agctaaagtt ttcgcattta tcgtgaaacg ctttcgcgtt    6240
tttcgtgcgc cgcttca                                                   6257
```

<210> SEQ ID NO 61
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61

```
cagttataaa gcaattgcag gaggaattgt ccgcgtaagg agatagcaat ggcgctg       57
```

<210> SEQ ID NO 62
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62

```
tacgcgaaag agttgtccaa ttgtgtttcc agccatcaga aagtctcctg ttcgatcac     59
```

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63

```
catcgctcat tcatccaggc                                                20
```

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64

```
tcgaggtcat gttgcaggtc                                                20
```

<210> SEQ ID NO 65
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65

-continued aaggagatag caatgattgc cttcgctcaa gttagtataa aaaagctgaa c    51

<210> SEQ ID NO 66
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
cagaaagtct cctgttctaa gcttgaagcc tgcttttttta tactaagttg g    51

<210> SEQ ID NO 67
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
atttgcgcac ggtattaact attttacacc aggcataagg agatagcaat gattgcctt    59

<210> SEQ ID NO 68
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ggctatcgga ttaccaaaaa cagcataggt ttccatcaga aagtctcctg ttctaagct    59

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
tggtgaagta tttggctcgg    20

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
aattgctgat gaatgaatgg cga    23

<210> SEQ ID NO 71
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide region between translationally coupled
      aroE and aroC genes

<400> SEQUENCE: 71
taaggagata gcaatggcgc tgttcgctca agttagtata aaaaagcagg cttcagtgat    60

```
cgaacaggag actttctga                                                    79
```

<210> SEQ ID NO 72
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide region between translationally coupled
      aroD and aroE genes

<400> SEQUENCE: 72

```
taaggagata gcaatgattg ccttcgctca agttagtata aaaaagcagg cttcaagctt       60
agaacaggag actttctga                                                    79
```

<210> SEQ ID NO 73
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73

```
taaggagata gcaatggcgc tgttcgctca agtta                                  35
```

<210> SEQ ID NO 74
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74

```
agcaggcttc agtgatcgaa caggagactt tctgatg                                37
```

<210> SEQ ID NO 75
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (14)..(76)

<400> SEQUENCE: 75

```
taaggagata gca atg gcg ctg ttc gct caa gtt agt ata aaa aag cag          49
                Met Ala Leu Phe Ala Gln Val Ser Ile Lys Lys Gln
                1               5                   10 gct tca gtg atc gaa cag gag act ttc tgatg                               81
Ala Ser Val Ile Glu Gln Glu Thr Phe
        15                  20
```

<210> SEQ ID NO 76
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

```
Met Ala Leu Phe Ala Gln Val Ser Ile Lys Lys Gln Ala Ser Val Ile
1               5                   10                  15

Glu Gln Glu Thr Phe
                20
```